US008952679B2

(12) United States Patent
Davis

(10) Patent No.: US 8,952,679 B2
(45) Date of Patent: Feb. 10, 2015

(54) PORTABLE SELF POWERED LINE MOUNTABLE ELECTRIC POWER LINE CURRENT MONITORING TRANSMITTING AND RECEIVING SYSTEM

(71) Applicant: Murray W. Davis, Grosse Pointe Woods, MI (US)

(72) Inventor: Murray W. Davis, Grosse Pointe Woods, MI (US)

( * ) Notice: Subject to any disclaimer, the term of this patent is extended or adjusted under 35 U.S.C. 154(b) by 0 days.

(21) Appl. No.: 14/059,483

(22) Filed: Oct. 22, 2013

(65) Prior Publication Data

US 2014/0176121 A1    Jun. 26, 2014

Related U.S. Application Data

(60) Provisional application No. 61/740,517, filed on Dec. 21, 2012.

(51) Int. Cl.
| | |
|---|---|
| *G01R 1/20* | (2006.01) |
| *H02G 1/02* | (2006.01) |
| *G01B 11/06* | (2006.01) |
| *G01W 1/14* | (2006.01) |
| *G01R 19/00* | (2006.01) |
| *G01R 31/08* | (2006.01) |
| *G01N 27/22* | (2006.01) |

(Continued)

(52) U.S. Cl.
CPC ........ *A64B 9/028* (2013.01); *H02G 1/02* (2013.01); *G01B 11/0616* (2013.01); *G01W 1/14* (2013.01); *G01R 1/20* (2013.01); *G01R 19/0092* (2013.01); *G01R 31/08* (2013.01); *G01N 27/223* (2013.01); *G01R 19/0084* (2013.01); *H01F 38/30* (2013.01); *H04N 5/2252* (2013.01); *G01D 11/30* (2013.01); *G01K 13/00* (2013.01); *H01F 27/02* (2013.01); *H01F 27/22* (2013.01); *H01R 4/28* (2013.01)
USPC .......................................................... 324/126

(58) Field of Classification Search
USPC ................................................. 324/126, 127
See application file for complete search history.

(56) References Cited

U.S. PATENT DOCUMENTS

| | | | |
|---|---|---|---|
| 2,303,824 | A | 12/1942 | Comins |
| 2,306,117 | A | 12/1942 | Dunlap |

(Continued)

FOREIGN PATENT DOCUMENTS

| | | | |
|---|---|---|---|
| CN | 2011-11-16 | | 11/2011 |
| CN | 202041573 | U * | 11/2011 |
| JP | 2003-061752 | | 9/2004 |

OTHER PUBLICATIONS

Rogowski coil, available at http://en.wikipedia.org/wiki/Rogowski_coil on Mar. 26, 2012.*

*Primary Examiner* — Melissa Koval
*Assistant Examiner* — Daniel Miller
(74) *Attorney, Agent, or Firm* — Carlson, Gaskey & Olds, P.C.

(57) ABSTRACT

A device for measuring current of an electric power line conductor includes a housing with an opening for accepting a power line conductor. A first coil loop including coil windings with a first end spaced from a second end and having a circular shape. The first coil loop is configured to partially surround the power line conductor located in the housing. An internal central wire attached to an end of the first coil loop extends through a center of the first coil loop. A jaw assembly is configured to insure a vertical centerline of the first coil loop is aligned with a vertical centerline of the electric power line conductor.

24 Claims, 18 Drawing Sheets

(51) Int. Cl.
*H01F 38/30* (2006.01)
*H04N 5/225* (2006.01)
*G01D 11/30* (2006.01)
*G01K 13/00* (2006.01)
*H01F 27/02* (2006.01)
*H01F 27/22* (2006.01)
*H01R 4/28* (2006.01)

(56) References Cited

U.S. PATENT DOCUMENTS

| | | | |
|---|---|---|---|
| 3,267,507 A | 8/1966 | Cox | |
| 3,622,867 A | 11/1971 | Topper et al. | |
| 3,861,197 A | 1/1975 | Adler | |
| 4,032,842 A | 6/1977 | Green et al. | |
| 4,052,000 A | 10/1977 | Honikman | |
| 4,061,963 A | 12/1977 | Green | |
| 4,234,863 A | 11/1980 | Shumway et al. | |
| 4,242,930 A | 1/1981 | Myers et al. | |
| 4,268,818 A | 5/1981 | Davis et al. | |
| 4,326,316 A | 4/1982 | Dolenti | |
| 4,420,752 A | 12/1983 | Davis et al. | |
| 4,546,340 A | 10/1985 | Kuchuris | |
| 4,728,887 A | 3/1988 | Davis | |
| 4,746,241 A * | 5/1988 | Burbank, III | 403/344 |
| 4,801,937 A | 1/1989 | Fernandes | |
| 4,806,855 A | 2/1989 | Davis | |
| 4,827,272 A | 5/1989 | Davis | |
| 5,029,101 A | 7/1991 | Fernandes | |
| 5,140,257 A | 8/1992 | Davis | |
| 5,232,518 A | 8/1993 | Nath et al. | |
| 5,341,088 A | 8/1994 | Davis | |
| 5,351,359 A | 10/1994 | Golden | |
| 5,426,360 A | 6/1995 | Maraio et al. | |
| 5,883,511 A | 3/1999 | Foster | |
| 6,151,065 A | 11/2000 | Steed et al. | |
| 6,157,160 A | 12/2000 | Okawa et al. | |
| 6,299,824 B1 | 10/2001 | Mayr et al. | |
| 6,713,670 B2 | 3/2004 | Stern et al. | |
| 6,741,069 B1 | 5/2004 | Klemar et al. | |
| 6,924,732 B2 | 8/2005 | Yahoo | |
| 6,983,508 B2 | 1/2006 | Saurer | |
| 7,030,593 B2 | 4/2006 | Pinkerton et al. | |
| 7,127,972 B2 | 10/2006 | Klein et al. | |
| 7,310,109 B2 | 12/2007 | Dottling et al. | |
| 7,412,338 B2 | 8/2008 | Wynans et al. | |
| 7,432,787 B2 | 10/2008 | Muench et al. | |
| 7,545,140 B2 | 6/2009 | Humphreys et al. | |
| 7,557,563 B2 | 7/2009 | Gunn et al. | |
| 7,570,045 B2 | 8/2009 | Wolfe et al. | |
| 7,579,824 B2 * | 8/2009 | Rea et al. | 324/117 R |
| 7,706,596 B2 | 4/2010 | Garvey | |
| 8,022,291 B2 | 9/2011 | Thomsen et al. | |
| 8,144,445 B2 | 3/2012 | Caggiano et al. | |
| 8,184,015 B2 | 5/2012 | Lilien et al. | |
| 8,203,328 B2 | 6/2012 | Bose et al. | |
| 8,300,922 B1 | 10/2012 | Garvey, III | |
| 8,320,146 B2 | 11/2012 | Haines et al. | |
| 8,322,332 B2 | 12/2012 | Rogers | |
| 8,400,504 B2 | 3/2013 | Al-Duwaish et al. | |
| RE44,256 E | 6/2013 | Bright et al. | |
| 8,536,857 B2 | 9/2013 | Nero, Jr. | |
| 8,628,211 B2 | 1/2014 | Jensen et al. | |
| 8,686,302 B2 | 4/2014 | Brasher et al. | |
| 2004/0012678 A1 | 1/2004 | Li | |
| 2006/0060007 A1 | 3/2006 | Mekhanoshin | |
| 2006/0125469 A1 | 6/2006 | Hansen | |
| 2008/0077336 A1 * | 3/2008 | Fernandes | 702/57 |
| 2008/0136403 A1 * | 6/2008 | Deck et al. | 324/110 |
| 2008/0297162 A1 * | 12/2008 | Bright et al. | 324/512 |
| 2009/0207421 A1 | 8/2009 | Kelly et al. | |
| 2009/0212241 A1 | 8/2009 | McGeoch | |
| 2009/0243876 A1 | 10/2009 | Lilien et al. | |
| 2010/0085036 A1 | 4/2010 | Banting et al. | |
| 2010/0192975 A1 | 8/2010 | Schweikert | |
| 2011/0204879 A1 | 8/2011 | Peretto | |
| 2011/0308566 A1 | 12/2011 | Johnson | |
| 2012/0086804 A1 | 4/2012 | Ishibashi et al. | |
| 2012/0152346 A1 | 6/2012 | Yang et al. | |
| 2013/0022078 A1 | 1/2013 | Phillips et al. | |
| 2013/0179079 A1 | 7/2013 | Lancaster | |
| 2014/0110376 A1 | 4/2014 | Zahlmann et al. | |

* cited by examiner

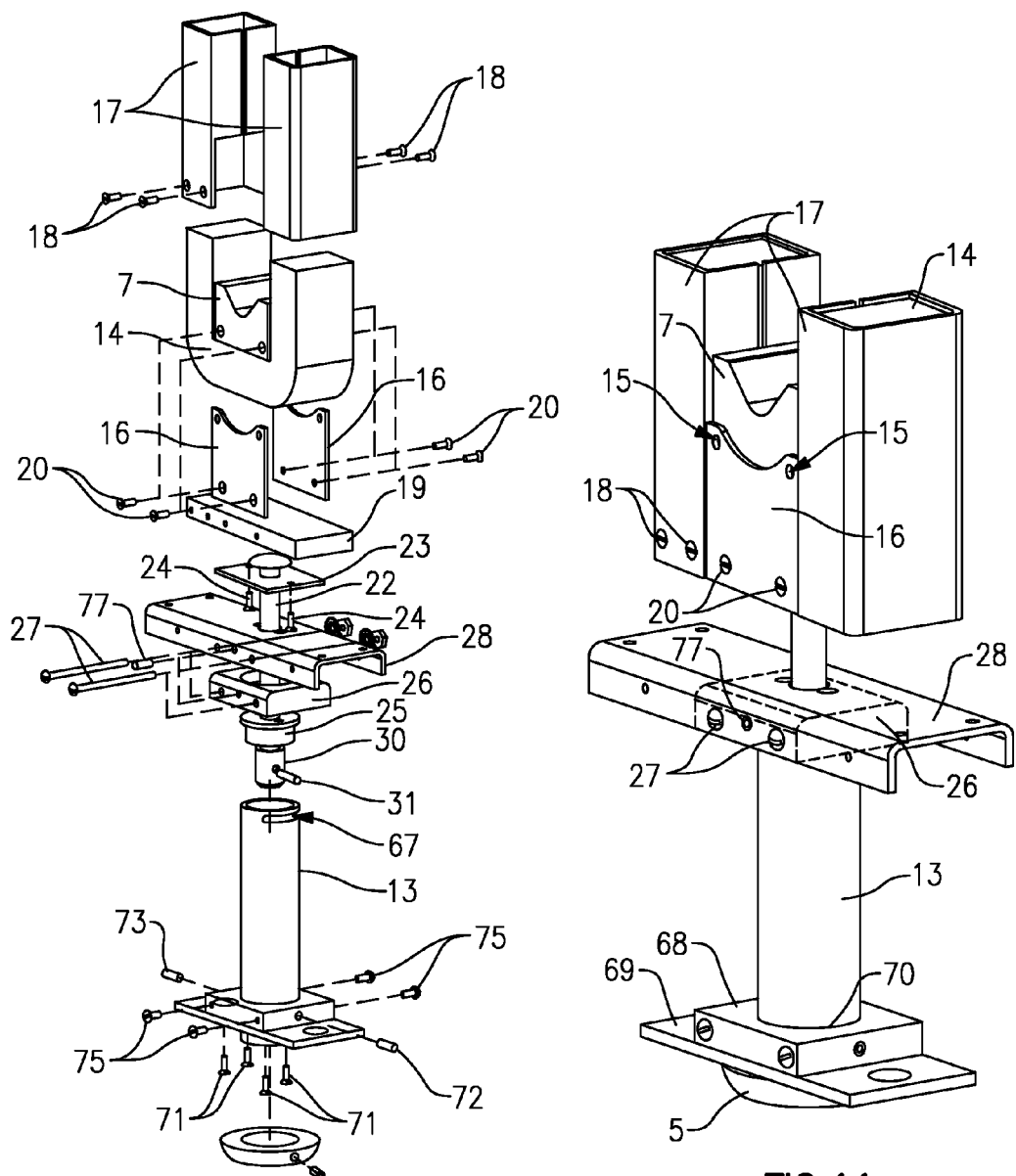

PORTABLE SELF POWERED LINE MOUNTABLE ELECTRIC POWER LINE CURRENT MONITORING TRANSMITTING AND RECEIVING SYSTEM

CROSS-REFERENCE TO RELATED APPLICATIONS

The application claims priority to U.S. Provisional Application No. 61/740,517 which was filed on Dec. 21, 2012.

BACKGROUND

The present disclosure relates to a multiple parameter sensor/transmitter-receiver unit which may be installed on or removed from an energized electric power line, such as an overhead power line. With the advent of Smart-Grid applications for electric power systems, there is an ever increasing need for a device that measures electric, mechanical, and environmental parameters of the power line.

In order to address the increasing need for monitoring power lines, devices have been developed that attach directly to the power line. These devices generally require a power source, such as batteries or solar panels. When utilizing batteries, regular maintenance must be performed to replace the batteries, which can become costly. When solar panels are used, the device may only be powered during sunny weather conditions and during daylight hours. Therefore, there is a need for a device that is powered from the current flowing in the electric power line conductor.

Additionally, utility companies invest significant capital into power systems and want to protect that investment from damage that could occur during faults, such as when trees fall onto power lines. Many prior art devices are capable of measuring current. However, the prior art devices require a coil winding to completely surround the power line to measure the power line frequency load current or fault current of the power line. This requires the power line to be disconnected to slip the coil around the power line, or a complex bending mechanism that bends the coil completely around the power line during installation or unbends the coil during removal which can lead to failure of the coil windings. Therefore, there is a need for a device which is low maintenance and can be constantly powered from the electric power line independent of weather conditions and still provide accurate current data without phase shift or saturation which is representative of the status of the power lines that is not susceptible to failure. Also, there is a need for a device that determines the direction of the fault current which may be opposite to the direction of the power line frequency load current, as well as a device that measures the high magnitude and high frequency of lightning stroke currents, and their location.

SUMMARY

A device for measuring current of an electric power line conductor includes a housing with an opening for accepting a power line conductor. A first coil loop including coil windings with a first end spaced from a second end and having a circular shape. The first coil loop is configured to partially surround the power line conductor located in the housing. An internal central wire attached to an end of the first coil loop extends through a center of the first coil loop. A jaw assembly is configured to insure a vertical centerline of the first coil loop is aligned with a vertical centerline of the electric power line conductor.

A method of determining a fault on a power line conductor includes determining the magnitude and direction of a load current waveform in the power line conductor with a loop coil and determining the magnitude and the direction of a fault current waveform in the power line conductor with the loop coil. A polarity of the fault current waveform is compared with a polarity of the load current waveform to determine if a change in polarity between the fault current waveform and the load current waveform has occurred to determine the direction of the fault. Data representing a fault is transmitted to at least one remote location if the predetermined trigger value is met.

These and other features of the disclosed examples can be understood from the following description and the accompanying drawings, which can be briefly described as follows.

BRIEF DESCRIPTION OF THE DRAWINGS

FIG. 10 illustrates an expanded view of the lower magnetic core, example lead screw assembly, and an example hotstick guide tube.

FIG. 11 illustrates the collapsed view of the lower magnetic core, the lead screw assembly, and the hotstick guide tube.

DETAILED DESCRIPTION

Figure 1:
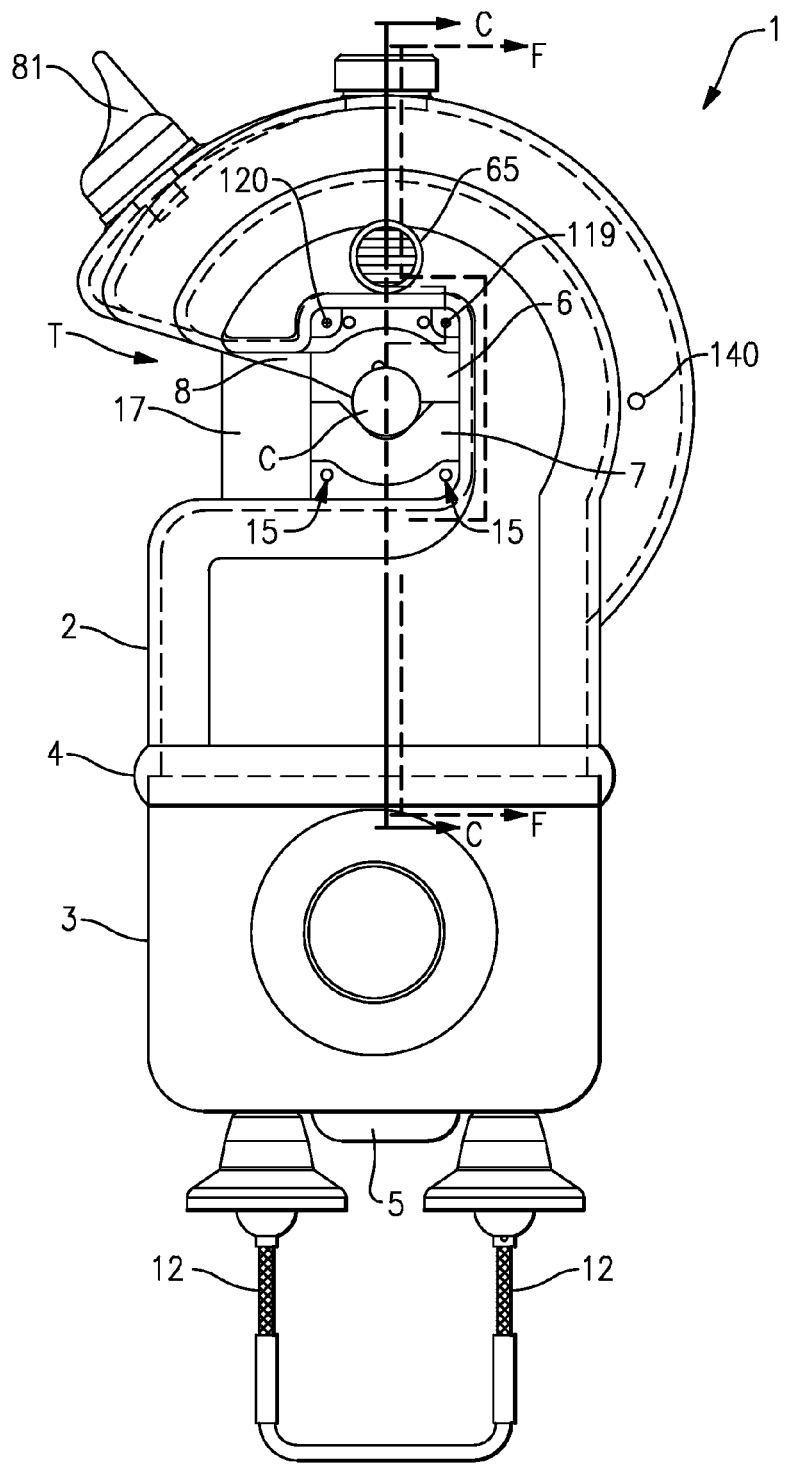
FIG. 1 illustrates a right side view of an example sensor transmitter receiver unit ("STR unit").
Figure 2:
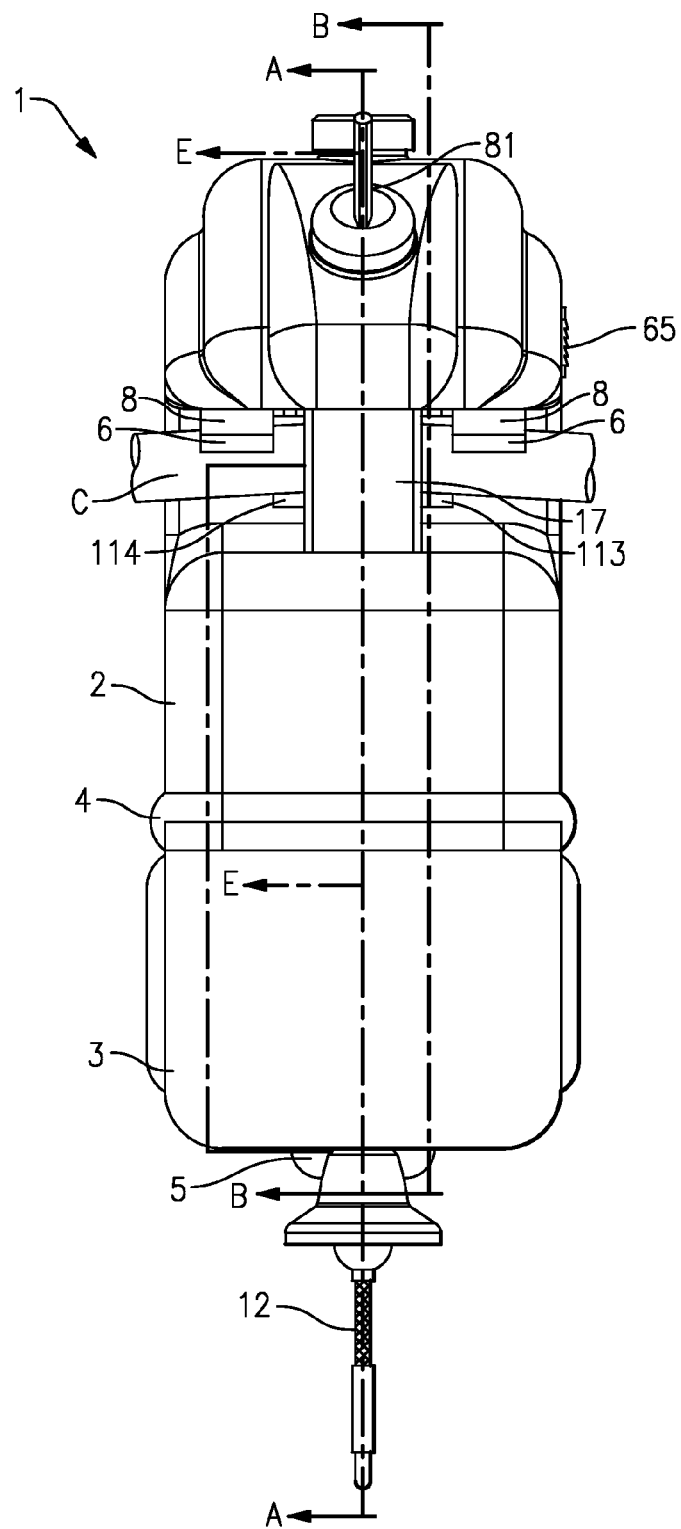
FIG. 2 illustrates a front view of the STR unit of FIG. 1.

FIGS. 1 and 2 illustrate an example sensor transmitter receiver unit ("STR unit") 1 installed on a power line conductor C for measuring and monitoring various parameters of the power line conductor C and its environment. The STR unit 1 is formed from a one piece upper housing 2 and a one piece lower housing 3. The lower housing 3 is accepted into a bead 4 formed on a distal end of the upper housing 2. In this example, the bead 4 which is an integral part of the upper housing 2 is formed by machining a portion of the upper housing 2 to form a groove on the inside of the bead 4. The lower housing 3 is secured to the bead 4 and the upper housing 2 by a collar 5. The collar 5 attaches to a hotstick guide tube 13 (FIG. 3) that is secured to the upper housing 2 and extends through the lower housing 3.

In one example, the upper housing 2 and the lower housing 3 are made of aluminum or other suitable electrically conductive material. The material chosen should accommodate subassembly installation without the use of external surface fasteners which could generate corona discharges due to high voltage being applied to the upper housing 2 and the lower housing 3. The upper housing 2 has the advantage of reducing the number of mating surfaces and eliminating mismatches between multiple cast parts which can generate corona discharges and audible noise due to slightly offset sharp edges of the mating surfaces of the adjacent castings.

Figure 3:
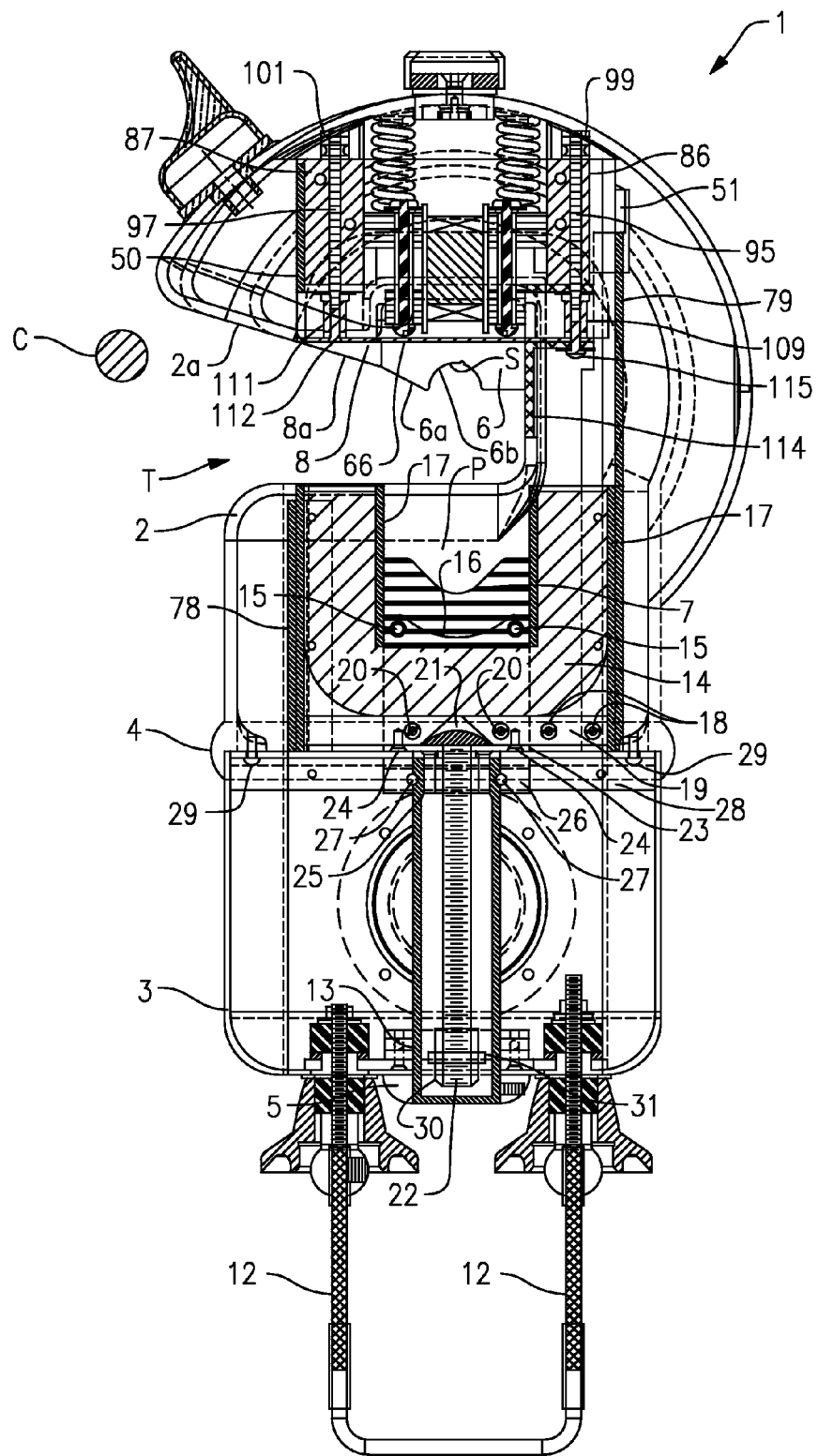
FIG. 3 illustrates a cross-sectional view taken along line A-A of FIG. 2.
Figure 4:
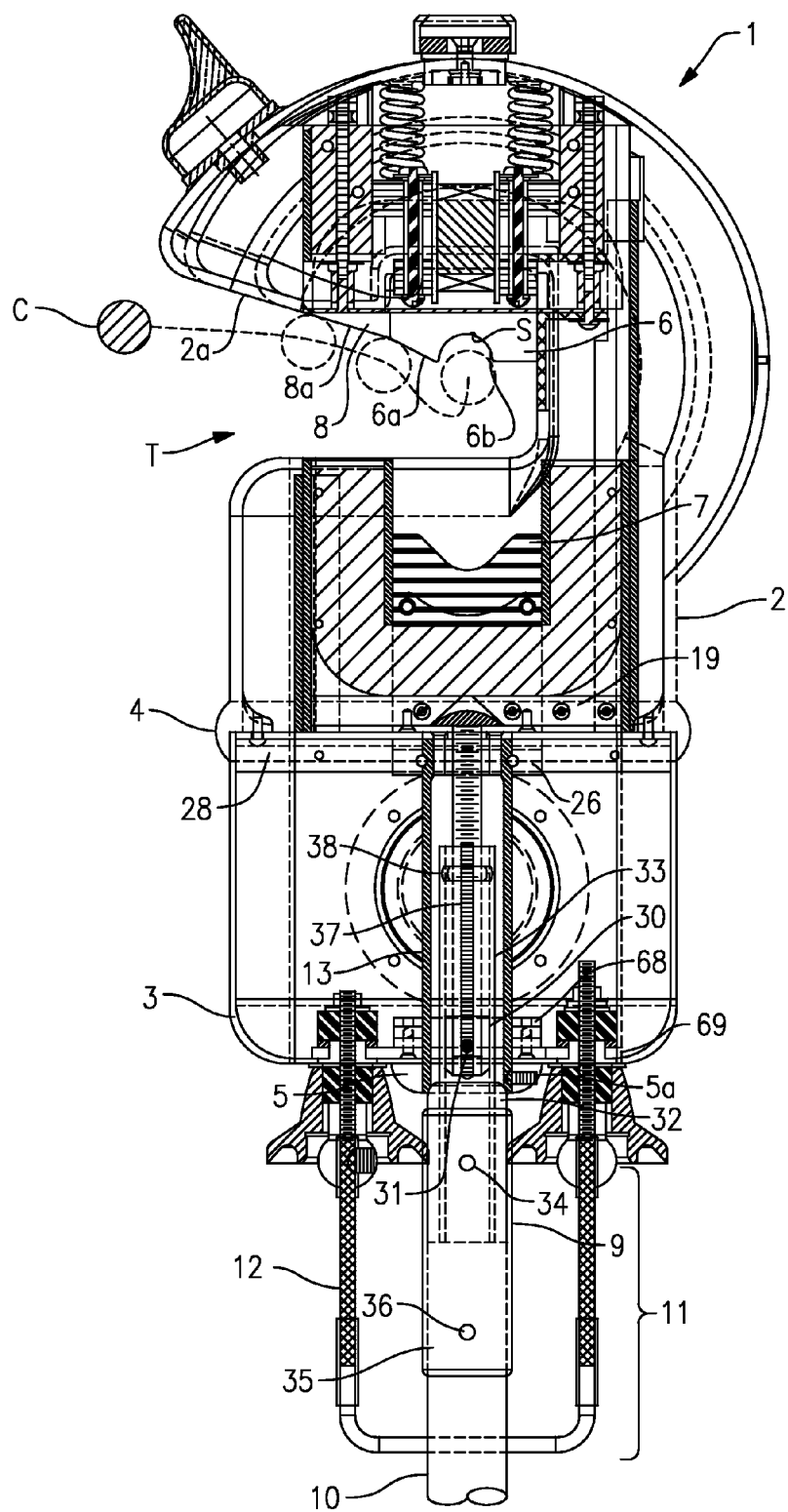
FIG. 4 illustrates a cross-sectional view taken along line A-A of FIG. 2 with an example hotstick.

Referring to FIGS. 3 and 4, before the STR unit 1 is clamped onto the conductor C, a lower jaw 7 is moved to its fully lowered position spaced from upper jaws 6. This allows the conductor C to pass from position "A" of FIG. 3 through a throat T on the left side of the upper housing 2 and onto the upper jaws 6 in position "B" as shown in FIG. 5.

With the lower jaw 7 of the STR unit 1 in its fully lowered position, a specially designed hotstick 10 is inserted into the bottom of the STR unit 1 and inside the hotstick guide tube 13. In this example, the hotstick 10 is made of an electrically insulated material such as fiberglass. The hotstick 10 includes a hotstick driver assembly 9 (FIG. 4) attached to the hotstick 10 with a pin 36. The hotstick 10 provides the required electrical insulation between the hands of the linemen and the energized conductor C. A flexible stirrup assembly 11 (FIG. 4) contains a flexible braided conductor 12 which bends out of the way to allow the hotstick driver assembly 9 to enter a hole in the collar 5. As mentioned earlier, the collar 5 secures the lower housing 3 to the bead 4 on the upper housing 2. The collar 5 is fastened to the hotstick guide tube 13 using the set screw 5a which is screwed into the collar 5 and into a hole in the hotstick guide tube 13.

With the hotstick 10 and the hotstick driver assembly 9 fully engaged inside the hotstick guide tube 13, the STR unit 1 can be lifted by the lineman with the hotstick 10 onto the conductor C while maintaining the STR unit 1 securely attached to the hotstick 10.

Figures 5, 5A:
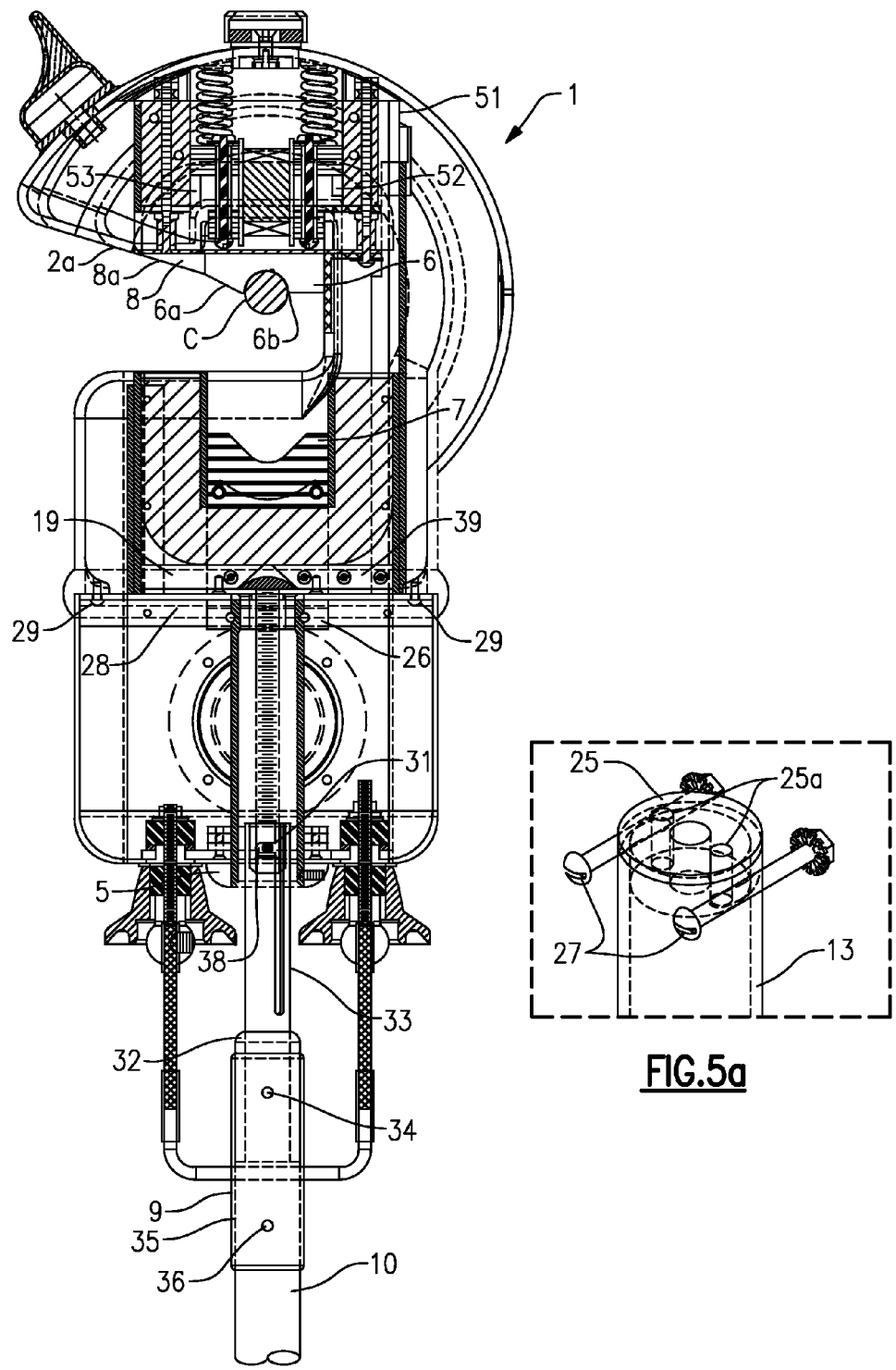
FIG. 5 illustrates another cross-sectional view taken along line A-A of FIG. 2 with the example hotstick.
FIG. 5a illustrates an enlarged view of a keyhole slot.
Figure 14:
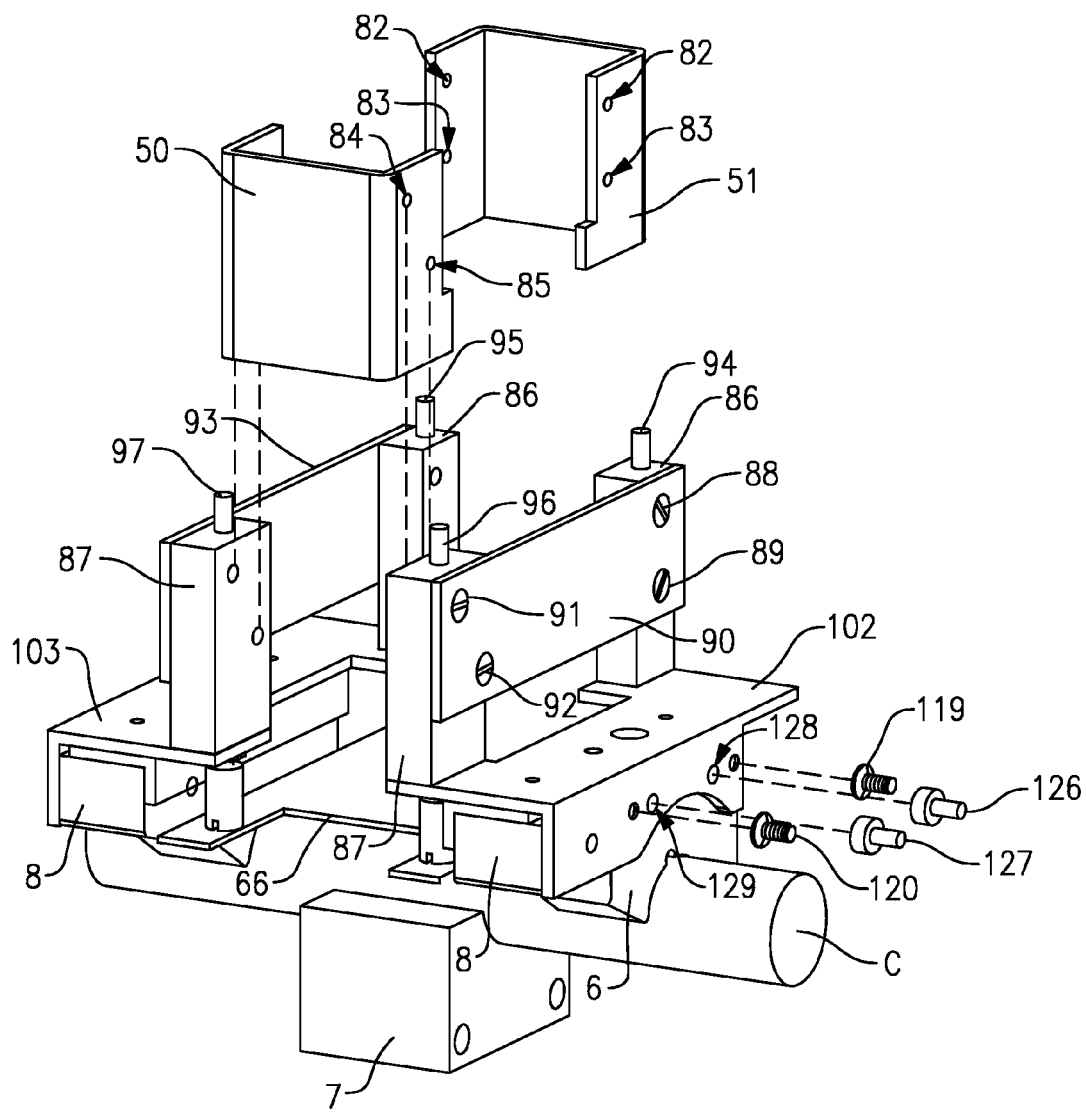
FIG. 14 illustrates an exploded view of example support blocks mounting the upper magnetic core subassembly and example upper and lower jaws.

The upper housing 2 includes two jaw inserts 8, shown in FIGS. 5 and 14, located adjacent the throat T and the upper jaws 6. The two jaw inserts 8 include inclined surfaces 8a and the upper jaws 6 include inclined surfaces 6a. The angle of incline of the inclined surfaces 8a matches the angle of the incline of an inclined surface 2a on the upper housing 2.

The angle of the inclined surfaces 6a is steeper than the angle of the inclined surfaces 8a and the inclined surface 2a to aid in installing the STR Unit 1 on the conductor C. As the conductor C slides across the inclined surfaces 2a and 8a and reaches the steeper incline of the inclined surface 6a, the STR unit 1 will bounce slightly upward and land in a circular notch 6b of the upper jaws 6 (See FIG. 4). This allows a conductor temperature sensor to be mounted vertically and in the middle inside the upper jaws 6 and initially extends slightly below the circular notch 6b for the upper portion of the conductor C. The two different inclined surfaces 6a and 8a of the jaw inserts 8 and upper jaws 6 prevent the conductor temperature sensor S, shown in FIGS. 3 and 4, from becoming damaged since the conductor C firmly lands vertically in the circular notch 6b of the upper jaws 6 and pushes the conductor temperature sensor S up to the inside surface of the circular notch 6b.

In FIG. 3, the lower jaw 7 is located in a pocket P between two legs of a lower magnetic core 14. The lower jaw 7 is held in place with two spring pins 132 and 133 (FIG. 15) located in the lower jaw 7 that snap into two holes 15 in a lower jaw holder 16 (FIGS. 10 and 11) which is attached to a bottom block 19 using two screws 20 (FIG. 3). The bottom block 19 is located adjacent the base of the upper housing 2.

Two identical electrically conductive lower core covers 17 partially surround the two legs of the lower magnetic core 14. The lower core covers 17 are attached to the bottom block 19 on each side of the lower jaw holder 16 using screws 18 of FIG. 3 on the front right side and one set of the screws 18 on the back left side (not shown). The front and back lower jaw holders 16 are both held in place by the four screws 20, two in the front and two in the back. The two legs of the lower magnetic core 14 are totally encased by the two lower core covers 17 and the front and back lower jaw holders 16. Therefore, the lower magnetic core 14 is not exposed to any moisture, such as from rain, snow, and ice that could enter through the throat T of the upper housing 2 (FIG. 3).

The bottom block 19 contains a conical hole 21 in the center which provides a very low friction bearing surface for the semi-circular top of a lead screw 22 (FIG. 3). The lead screw 22 is held in the conical hole 21 with a retainer plate 23 which has a hole in the middle the size of the lead screw 22 diameter and is fastened to the bottom block 19. The lead screw 22 is threaded into the center of a threaded bushing 25. The threaded bushing 25 has a reduced diameter cylindrical lower portion which fits inside the hotstick guide tube 13 and a larger diameter cylindrical top portion of the threaded bushing 25 is supported on the upper end of the hotstick guide tube 13. Both the threaded bushing 25 and the hotstick guide tube 13 are attached to a hotstick guide support 26 using two large through bolts 27 and nuts which are placed through the holes in a bottom support 28.

Referring to FIG. 2, the upper jaws 6 include two spaced apart jaws and the lower jaw 7 includes a single jaw aligned between the two spaced apart upper jaws 6. When lower jaw 7 is clamped onto the conductor C, the conductor C is bent slightly upward as the lower jaw 7 extends upward between the upper jaws 6 creating a bending moment in the conductor C. The bending moment in the conductor C prevents the STR unit 1 from sliding down the conductor C, especially when the STR unit 1 is mounted at the point of attachment adjacent a utility pole or tower where the slope of the conductor C is at its maximum value. Preventing the upper jaws 6 and the lower jaw 7 from sliding down the conductor C at the point of attachment is necessary when the STR unit is being used to measure sag of the power line conductor.

Referring to FIGS. 5 and 5a, the bottom support 28 includes an upside down "U" shaped cross member and is fastened at each end to the upper housing with two large threaded screws 29 on each side. The threaded bushing 25 has two small vertical holes 25a drilled through the threaded bushing 25 on each side of the threaded hole in the middle for the lead screw 22. The vertical holes 25a are countersunk on the top and provide drainage paths for water that can accumulate underneath the bottom block 19 and on top of the bottom support 28 (FIG. 5a). The water then drains through the two vertical holes 25a in the threaded bushing 25 and drops on the inside of the hotstick guide tube 13 and out the bottom of the STR unit 1. Therefore, water will not leak into the lower housing 3.

Figure 6:
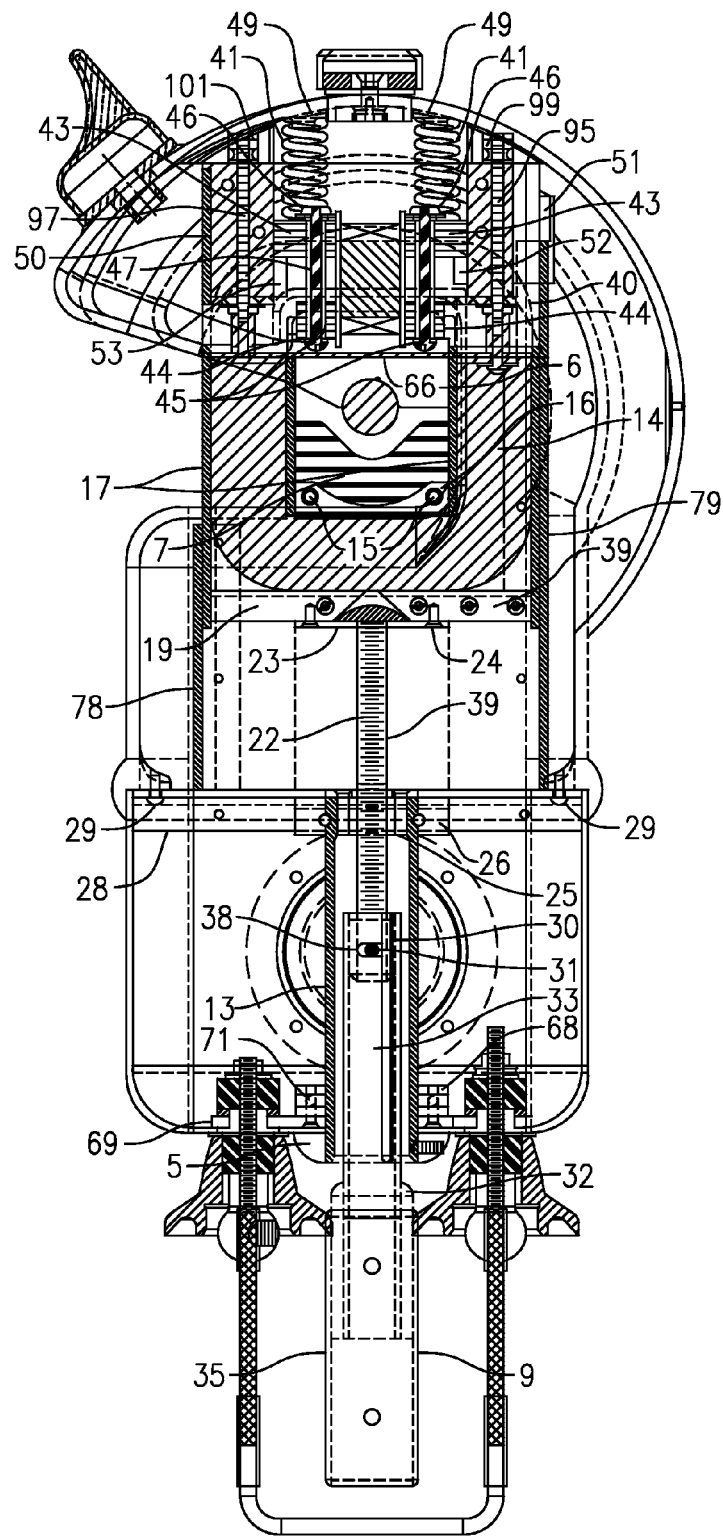
FIG. 6 illustrates another cross-sectional view taken along line A-A of FIG. 2 engaging a conductor.

Referring to FIG. 6, the lead screw 22 has a small diameter hotstick guide 30 which is threaded on the inside and is screwed on the bottom of the lead screw 22. A pin 31 keeps the hotstick guide 30 from turning on the lead screw 22. The hotstick guide 30 prevents the inside of a hotstick lead screw driver 33 from coming into contact with the threads on the lead screw 22 and damaging the internal bore of the lead screw driver 33. It also guides the lead screw driver 33 onto the lead screw 22. When the pin 31 engages the lead screw driver 33 the STR unit 1 is ready for installation on the conductor C.

The hotstick driver assembly 9 includes the lead screw driver 33, a hotstick driver coupling 32, a rivet 34, a hotstick sleeve 35, the pin 36, and the hotstick 10. The hotstick 10 of FIG. 4 rests on the rounded portion of the hotstick driver coupling 32 and the rounded inside bottom of the hotstick guide tube 13. This prevents the lead screw driver 33 from applying pressure to the threaded bushing 25 upon installation of the STR unit 1 on the conductor C. The lead screw driver 33 and the hotstick driver coupling 32 are each fastened to the hotstick sleeve 35 by the rivet 34 and the hotstick sleeve 35 is attached to the hotstick 10 with the pin 36. A long narrow vertical slot in the lead screw driver 33 allows the pin 31 of the lead screw 22 to be engaged with the lead screw driver 33 and is free to slide up or down in the vertical slot 37 as the lead screw is turned to tighten the lower jaw 7 on the conductor C or to loosen the lower jaw 7 from the conductor C to remove the STR unit 1.

When the hotstick driver assembly 9 is engaged with the lead screw 22 as shown in in FIG. 4, the STR unit 1 is raised to position "A" relative to the height of the conductor C. The STR unit 1 is then moved toward the conductor C so that the conductor C passes through the throat T of the upper housing 2 and into position "B" as shown in FIG. 5. Once the STR unit 1 is fully supported by the conductor C in position "B", the hotstick driver assembly 9 is turned clockwise by the installer with the hotstick 10 and allowed to drop down from its position in FIG. 4 to a lower position as in FIG. 5. A horizontal keyhole slot 38 of the lead screw driver 33 is now engaged with the pin 31 of the lead screw 22. With the pin 31 in the horizontal keyhole slot 38, the hotstick driver assembly 9 and the hotstick 10 are secured to the STR unit 1.

In this example, an opening and closing mechanism 39 of FIG. 6 extends the lower jaw 7 upward to secure the STR unit 1 on the conductor C. Additionally, the opening and closing mechanism 39 can also retract the lower jaw 7 to remove the STR unit 1 from the conductor C. The opening and closing mechanism 39 includes the lower magnetic core 14, the lower core covers 17, the lower jaw holders 16, the lower jaw 7, spring pins 132 and 133, the bottom block 19, the retainer plate 23, two fasteners 24, the lead screw 22, the hotstick guide 30, and the pin 31.

FIG. 6 illustrates the keyhole slot 38 on the lead screw driver 33 engaged with the pin 31 on the lead screw 22. As the lead screw 22 is turned clockwise, the opening and closing mechanism 39 moves the lower magnetic core 14 toward an upper magnetic core 40. The upper magnetic core 40 has two large compression springs 41 to bias the upper magnetic core 40 downward. The compression springs 44 provide pressure to hold both the upper magnetic core 40 and the lower magnetic core 14 together to reduce the magnetic reluctance caused by air gaps 54 (FIG. 8) between the upper magnetic core 40 and the lower magnetic core 14.

The hotstick driver assembly 9 can continue to be turned clockwise even after the lower magnetic core 14 begins to mate with the upper magnetic core 40 because the compression springs 41 compress at the top of the upper magnetic core 40. The clockwise motion of the hotstick driver assembly 9 can be achieved either manually or with a battery powered drill or another rotating device, until the lower jaw 7 is tightened onto the conductor C. After the STR unit 1 is mounted on the conductor C, the hotstick 10 is turned slightly to the left, or counterclockwise, and the pin 31 will become disengaged from the horizontal portion of the keyhole slot 38. The hotstick 10 is then free to be removed when the pin 31 aligns with the vertical slot 37.

Figure 7:
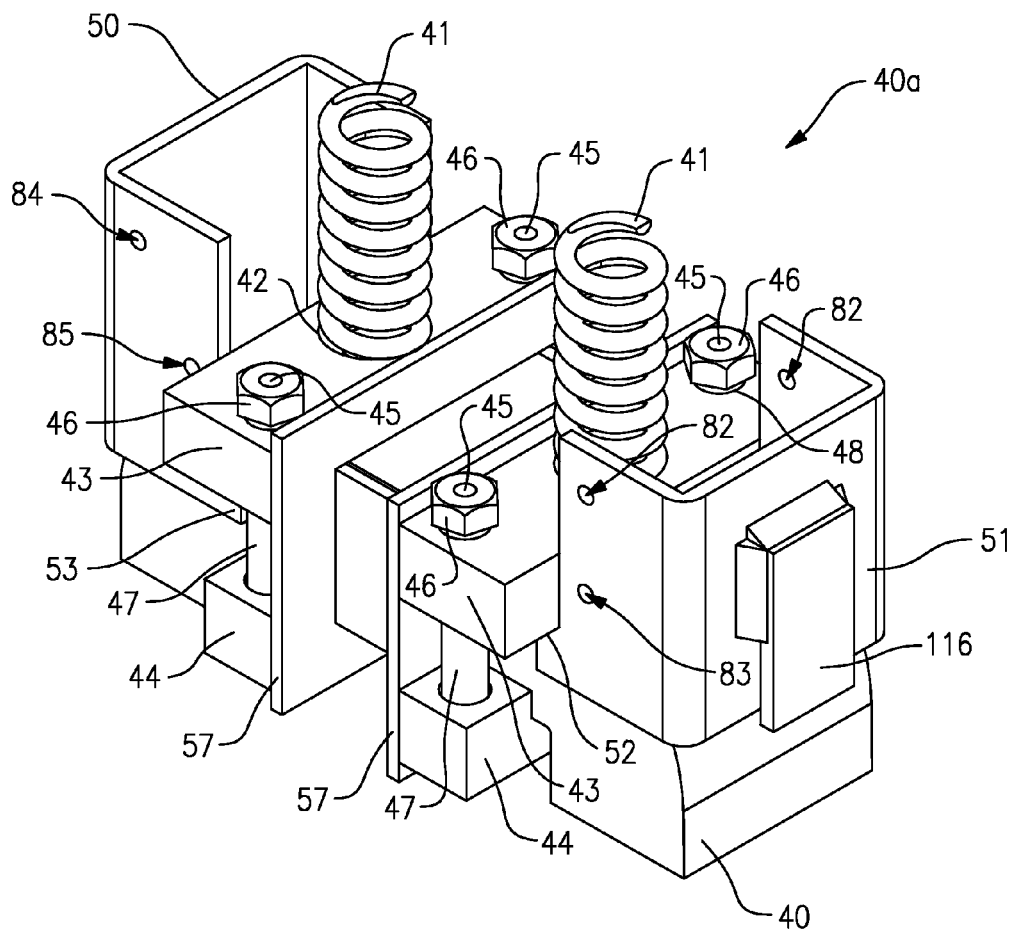
FIG. 7 illustrates an example upper magnetic core subassembly.
Figure 8:
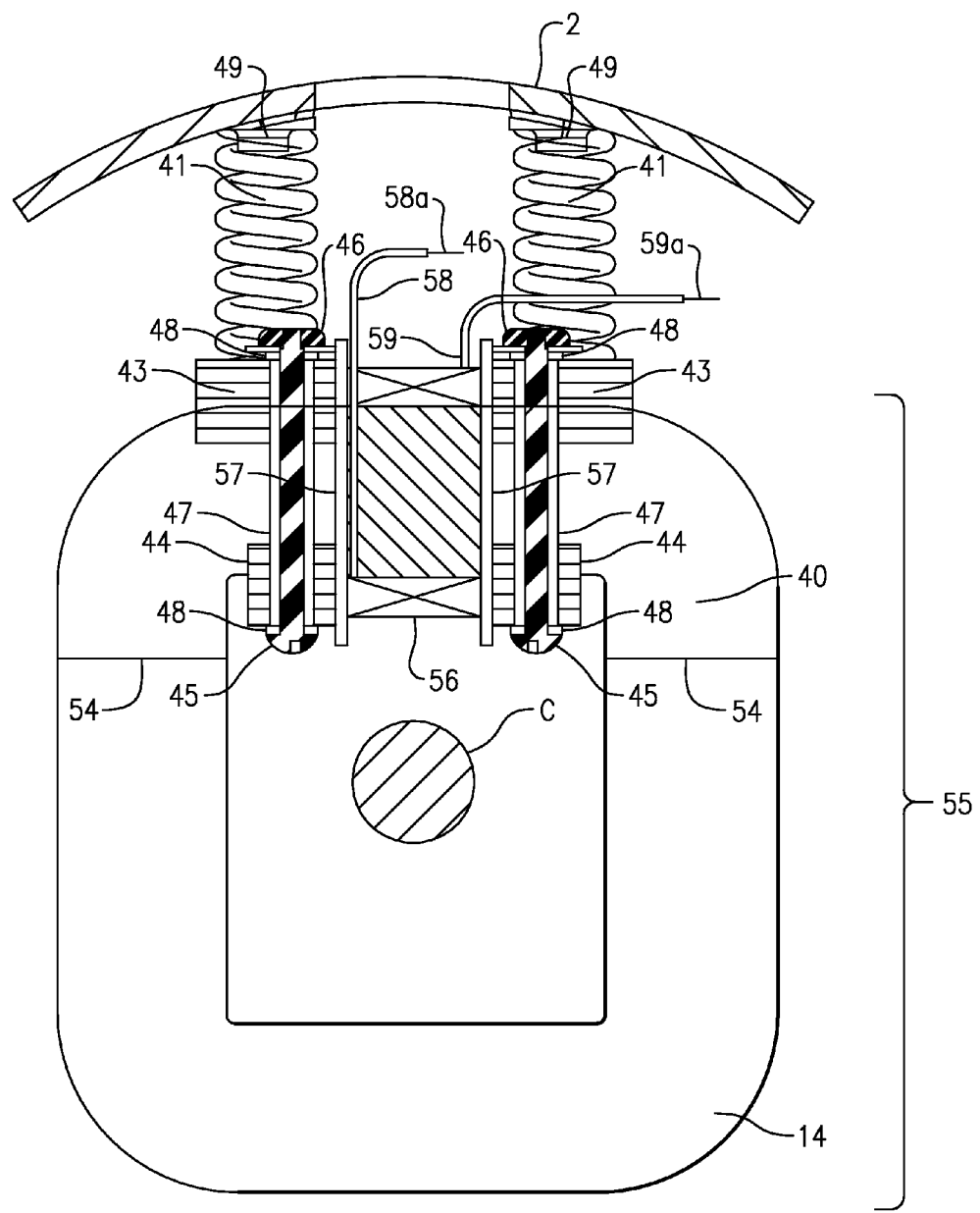
FIG. 8 illustrates an expanded view of an example upper magnetic core and an example lower magnetic core surrounding the conductor and an example power supply transformer.

FIGS. 7 and 8 illustrate the bottom of the compression springs 41 are held in alignment in two cylindrical pockets 42 of two identical horizontal upper core blocks 43 which are each used to clamp the upper magnetic core 40 to two identical magnetic horizontal lower core blocks 44. The top of the compression springs 41 are held in place with two projections 49 extending downward on the inside of the upper housing 2. The compression springs 41 are totally enclosed by the upper housing 2 and are protected from the adverse weather which can cause corrosion. The air gaps 54 between the upper and lower magnetic cores 40 and 14 are totally enclosed by the upper housing 2 which prevents the air gaps 54 from becoming corroded due to moisture from the environment. The horizontal upper core blocks 43 and the horizontal lower core blocks 44 are clamped around the upper magnetic core 40 on each side using two through bolts 45 and two nuts 46 in the front and two through bolts 45 and two nuts 46 located in the back of the upper horizontal core blocks 43 and horizontal lower core blocks 44.

When the two large compression springs 41 push the upper core blocks 43 down, the upper magnetic core 40 is prevented from falling out of a left core shoe 50 and a right core shoe 51, by a step 52 located at the bottom of the right core shoe 51 and a step 53 located at the bottom of the left core shoe 50.

When the lower magnetic core 14 mates with the upper magnetic core 40, the lead screw 22 can be turned further clockwise to move the two upper core blocks 43 away from the steps 52 and 53 and further compress the compression springs 41. The lead screw 22 can continue to be turned clockwise and compress the compression springs 41 until the lower jaw 7 and the upper jaws 6 are tight on the conductor C.

Electrical insulating spools 47 are inserted over each of the through bolts 45 and electrical insulating washers 48 are inserted under the head of each through bolt 45 and under each nut 46. The insulating spools 47 and the insulating washers 48 on each of the through bolts 45 prevent shorted electrically conductive paths around the upper magnetic core 40 which is comprised of the four through bolts 45, four nuts 46, the two electrically conductive upper core blocks 43 and the two lower core blocks 44.

When the upper jaws 6 and the lower jaw 7 are firmly tightened on the conductor C, the compression springs 41 are compressed to their maximum distance, and thus the maximum compressive force is also applied to the lower magnetic core 14 and the upper magnetic core 40. This decreases the size of the air gaps 54 between the lower magnetic core 14 and the upper magnetic core 40 and the magnetic reluctance between the lower magnetic core 14 and the upper magnetic core 40. Depending on the size of the conductor C, varying amounts torque can be applied to the hotstick driver assembly 9 to tighten the opening and closing mechanism 39 on the conductor C.

The physical size and shape of the upper jaws 6 and the lower jaw 7 are designed such that approximately the same compressive force is applied to the upper magnetic core 40 and the lower magnetic core 14. In one example, there are five different sets of upper and lower jaws 6 and 7 that can fit different conductor sizes and types ranging from 0.162 inches in diameter and up to 1.17 inches in diameter. The opening and closing mechanism 39 allows the STR unit 1 to be installed on a wide range of conductor diameters without changing the upper jaws 6 and the lower jaws 7 while maintaining sufficient contact between the upper magnetic core 40 and the lower magnetic core 14 to complete the magnetic circuit of the power supply transformer 55 of the STR unit 1 which derives its power from the current flowing through the conductor C to power a power supply module 60 of FIG. 9. Because the STR unit 1 derives power from the conductor C, batteries or solar cells are not required to power the STR unit 1. The STR unit 1 is powered at all times when current is flowing in the conductor C, even at current levels as low as 6.8 amperes and still process data and transmit data at 1 watt power levels because of the low threshold of the power supply module 60.

Maintaining a minimum magnetic reluctance insures that a power supply transformer 55 (FIGS. 8 and 9) will provide the needed secondary voltage V2 and secondary current I2 to operate the power supply transformer 55, sensor electronics module 63, and transmitter/receiver 64. The power supply transformer 55 includes the upper magnetic core 40, the lower magnetic core 14, and a coil winding 56. The upper magnetic core and the lower magnetic core form a window W for accepting the conductor C.

Figure 12:
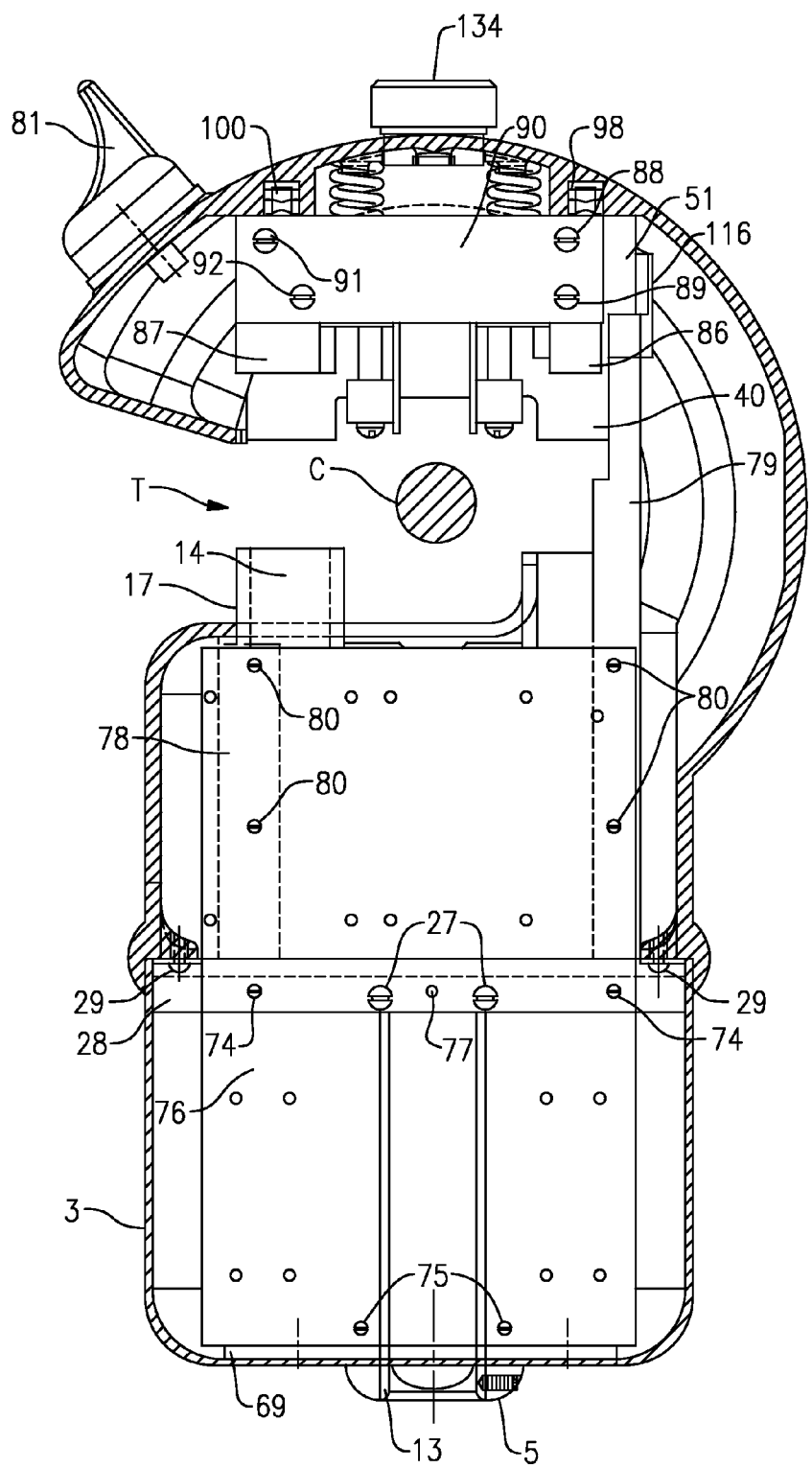
FIG. 12 illustrates a cross-sectional view taken along line B-B of FIG. 2.

The number of secondary turns N2 of wire on the coil winding 56 are optimized to produce the required secondary voltage V2 and secondary current I2 with a minimum of current I1 in the conductor C. The coil winding 56 is held in place by two coil bobbins 57 which are supported laterally by the two upper core blocks 43 and the two lower core blocks 44. Secondary leads 58a and 59a of coil windings 58 and 59, respectively, are connected to the power supply module 60 which maintains the same level of secondary voltage across leads 61 and 62 for the sensor electronics module 63 and the transmitter/receiver 64 even though the primary current may range from 34 amperes up to 1000 amperes. Lower primary currents of 6.8 amperes are achievable with the low threshold current power supply module 60. The power supply module 60 contains an energy storage device 256 (FIG. 13) which can power the transmitter/receiver 64 when the conductor C current ceases to flow. A transmitting and receiving antenna 81 for the on-board transmitter/receiver 64 is mounted on the upper housing 2 (FIG. 12).

Locating the coil winding 56, 58, and 59 on the upper magnetic core 40 allows the heat from the coil winding 56, 58, and 59 to escape through a vent 65 (FIG. 1) in the upper housing 2. When the conductor sensor S located within the STR unit 1 measures the temperature of the conductor C, it is important that the heat from the coil windings 56, 58, and 59 does not affect the temperature of the conductor C or the conductor temperature sensor S, which is in electrical communication with the sensor electronics module 63. As shown in FIG. 6, a thermally insulating barrier 66 located below the coil windings 56, 58, and 59, allows for a more accurate temperature reading of the conductor temperature by blocking heat from the coil windings 56, 58, and 59.

FIGS. 10-12 and 13 illustrate the lower magnetic core 14 with the lower core covers 17, the lead screw 22, the hotstick guide tube 13, and other related parts in both exploded and collapsed views. The hotstick guide tube 13 is anchored at the top with the through bolts 27 that extend through the bottom support 28 and the hotstick guide support 26. A round cylindrical milled slot 67 is located along opposing sides of the top of the hotstick guide tube 13 to accept the through bolts 27 that support the hotstick guide tube 13.

A central hole 70 extends through a base plate support 68 and a base plate 69 for accepting a bottom portion of the hotstick guide tube 13. The base plate support 68 and the base plate 69 are connected to each other with four identical threaded screws 71. The hotstick guide tube 13 is attached to the base plate support 68 and the base plate 69 with set screws 72 and 73. Left and right side panels 76 of FIG. 12 are attached to the base plate support 68 and the bottom support 28 for the lower core 14 with the use of two identical screws 74 extending through the bottom support 28 and the side panel 76 and at the bottom with two identical screws 75 extending through the side panel 76 and the base plate support 68.

The threaded bushing 25 rests on top of the hotstick guide tube 13 and is prevented from turning relative to the hotstick guide tube 13 using a set screw 77. The left and right side panels 76 not only provide added strength, but also provide the physical space to mount the power supply module 60, the transmitter/receiver 64, the sensor electronics 63, and support left and right lower core guides 78 and 79.

The left lower core guide 78 and a right lower core guide 79 are "U" shaped and guide the opening and closing mechanism 39 such that the lower magnetic core 14 is aligned with the upper magnetic core 40. Each of the left and right lower core guides 78 and 79 are attached to the left and right side panels 76 with four threaded screws 80. The lower housing 3 is placed over the hotstick guide tube 13 at the bottom and fitted up to the base plate 69 and held in place with the collar 5. This means that once the collar 5 is removed, the lower housing 3 can be removed thus allowing access to the power supply module 60, sensor electronics module 63, and the transmitter/receiver 64 of FIG. 9 mounted inside and on the left and right side panels 76 for easy maintenance and repair.

FIGS. 7 and 12-15 illustrate an upper magnetic core subassembly 40a mounted to the upper housing 2. The left and right core shoes 50 and 51 support the upper magnetic core 40 such that the upper magnetic core 40 can move freely up and down inside the left and right shoes 50 and 51. The left and right core shoes 50 and 51 are attached to the upper housing 2 using four support blocks 86 and 87 of FIG. 14, right and left upper core guides 90 and 93, and four vertical through bolts 94, 95, 96, and 97.

Figure 13:
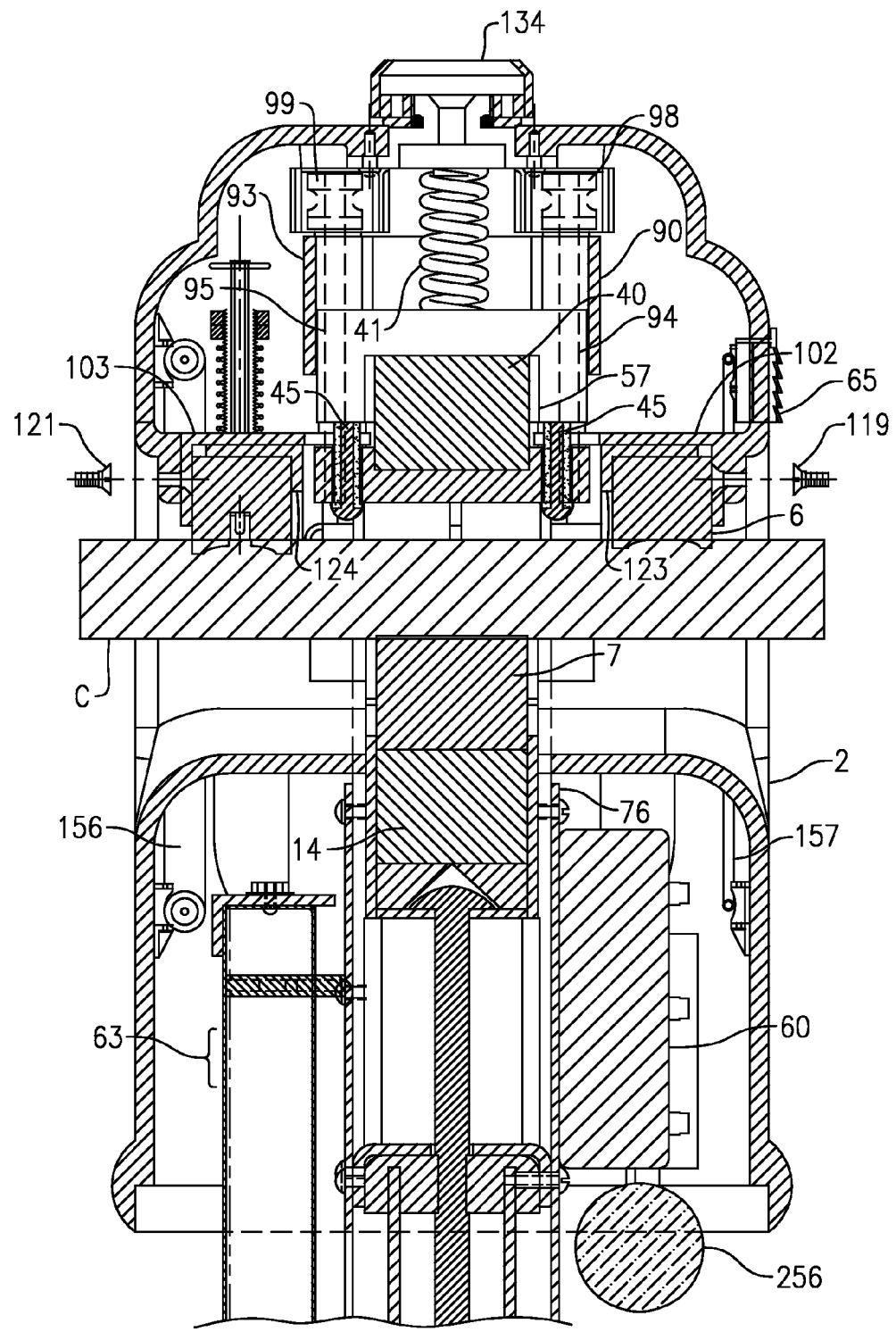
FIG. 13 illustrates a cross-sectional view taken along line C-C of FIG. 1.
Figure 16:
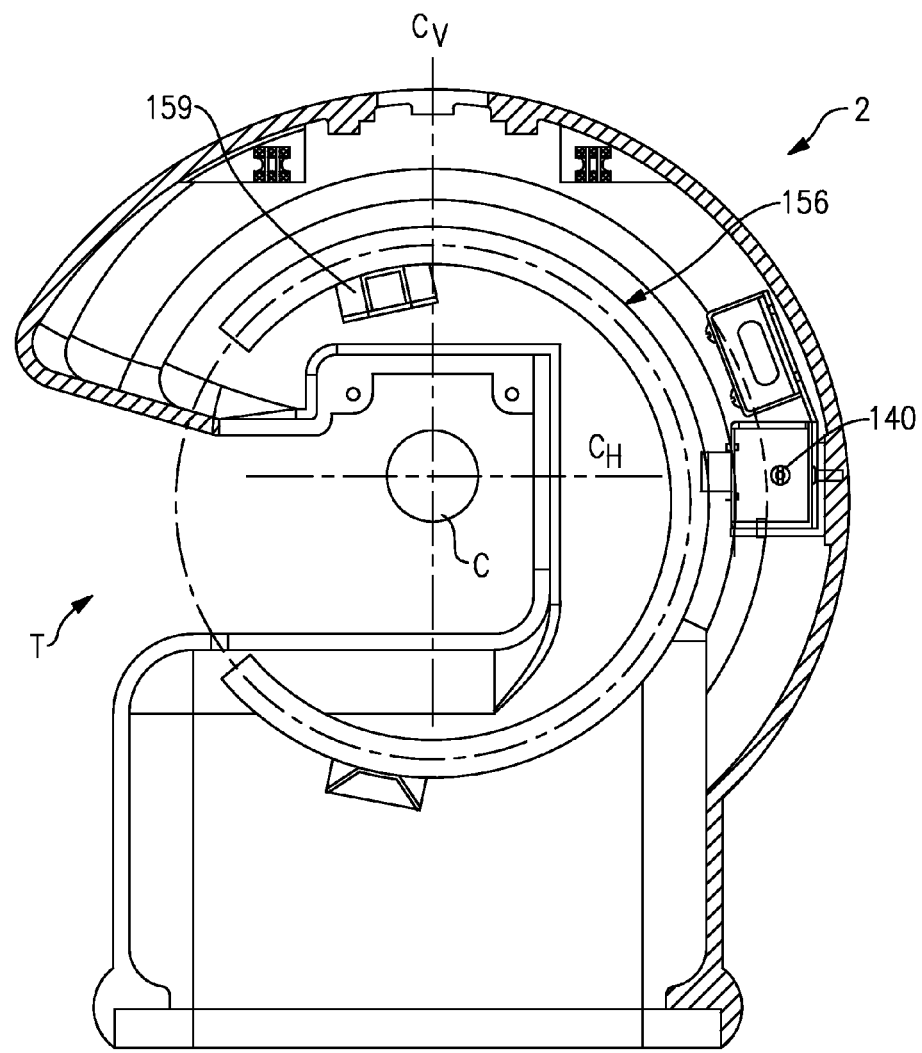
FIG. 16 illustrates a cross-sectional view of an example upper housing including an example "C" loop coil for measuring the power line frequency current taken along line E-E of FIG. 2.

The upper magnetic core subassembly 40a can be inserted through the throat T and fastened to the inside of the upper housing 2. A top portion of the upper housing 2 is "C" shaped which provides a surface on the inside for mounting a "C" loop coil 156 for measuring the power line frequency current (60 Hz or 50 Hz) and a "C" loop coil 157 for measuring lightning stroke current of 200 kA or higher (FIGS. 13 and 16).

The right core shoe 51 has two identical threaded holes 82 and 83 on the front and back for a total of four, and left core shoe 50 has two identical threaded holes 84 and 85 on the front and back for a total of four as shown in FIGS. 7 and 14. As shown in FIG. 14, two identical support blocks 86 on the right side are placed on the front and back of the right core shoe 51 and two identical support blocks 87 are placed on the front and back of the left core shoe 50.

To align the two right side support blocks 86 with the two sets of threaded holes 82 and 83 on the right side of the right core shoe 51, threaded screws 88 and 89 are first inserted into the upper and lower holes in the right side upper core guide 90 and then through the two holes in the right support block 86 and screwed into the accommodating threaded holes 82 and 83 of the right core shoe 51. The two left side support blocks 87 are held in alignment with the left core shoe 50 by first inserting two threaded screws 91 and 92 through the other end of the right side upper core guide 90 and then through the holes in the left side support block 87 and screwed into the threaded holes 84 and 85 of the left core shoe 50. The same process is repeated on the back side by connecting support blocks 86 and 87 to the left upper core guide 93 with the backside of the right core shoe 51 and the back side of the left core shoe 50.

The purpose of the upper core guides 90 and 93 is to insure the two long vertical through bolts 94 and 95 placed through the vertical holes in the two right side support blocks 86 and two long vertical through bolts 96 and 97 placed through the vertical holes in the two left side support blocks 87 line up with the four threaded holes in four threaded inserts 98, 99, 100, and 101, which are embedded in the casting of the upper housing 2. The two right side support blocks 86 are prevented from falling down by inserting the back of a right side upper jaw holder 102 and the back of the left side upper jaw holder 103 over the vertical through bolts 94 and 95 and threading nuts 104 and 105 onto the two vertical through bolts 94 and 95 and tightening them down, respectively. The two left side support blocks 87 are held in place by inserting the vertical through bolts 96 and 97 through the front hole in the right side upper jaw holder 102 and the front hole in the left side upper jaw holder 103 and threading two nuts 106 and 107 on the vertical through bolts 96 and 97 and tightening them down, respectively.

Four threaded through standoffs 108, 109, 110, and 111 are screwed onto the four vertical through bolts 94, 95, 96, and 97, respectively. The thermal barrier 66 is placed over the four bottom holes of the standoffs 108, 109, 110, and 111 and screwed to the standoffs 110 and 111 on the front left side with two flat head screws 112 as shown in FIG. 15.

Figure 15:
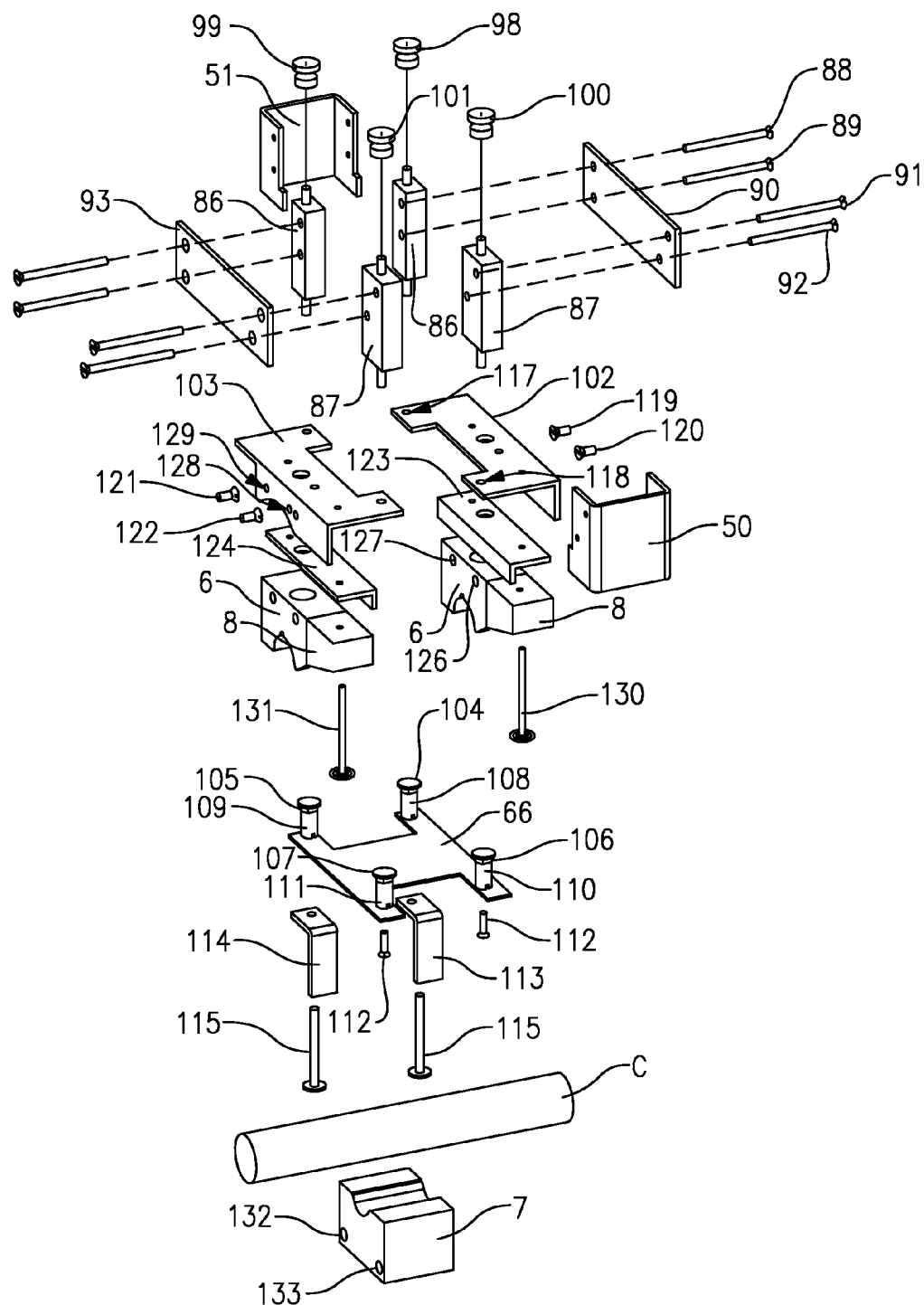
FIG. 15 illustrates an exploded view of an upper magnetic core mount and the upper and lower jaws.

FIGS. 2 and 15 illustrate casting fillers 113 and 114 located on the back left and back right sides of the STR unit 1 and secured with round head screws 115 which are first inserted through holes in the casting fillers 113 and 114 and then through the two back holes on the right and left side of the thermal barrier 66 and into the standoffs 108 and 109, respectively.

After the upper magnetic core subassembly 40a is mounted, the left and right lower core guides 78 and 79 including the opening and closing mechanism subassembly 39 and the left and right side panels 76 are inserted through the bottom of the upper housing 2. (See FIG. 12). Four screws 29 are inserted through the two holes on the left and the two holes on the right of the bottom support 28 and screwed into the threaded holes of the upper housing 2. It should be noted that during the insertion process, the right lower core guide 79, shown in FIG. 12, slides around the outside surface of the right core shoe 51 and underneath a tab 116 at the top as a weldment on the right upper side of the right core shoe 51.

As shown in FIG. 12, the tab 116 insures that the right lower core guide 79 fits precisely around the outside of the right core shoe 51 to provide a near perfect alignment of the lower magnetic core 14 with the upper magnetic core 40. The precise alignment between the upper magnetic core 40 and the lower magnetic core 14 reduces magnetic reluctance by decreasing the air gaps 54. This results in a decrease in the threshold current for the operation of the power supply module 60.

Referring to FIGS. 14 and 15, the right side upper jaw holder 102 and the left side upper jaw holder 103 support the two upper jaws 6 and the jaw inserts 8. The long vertical through bolts 96 and 97 which are screwed into the threaded inserts 100 and 101 at the top and on the inside of the upper housing 2 fit through top holes 117 and 118 on the back and front of the right side upper jaw holder 102 on the right side. Also, flush mount screws 119 and 120 are inserted on the back and through corresponding holes in the right side upper jaw holder 102 and are screwed into the upper housing. The flush mount screws 119 and 120 are installed before the upper jaws 6 and inserts 8 are mounted to the right side upper jaw holder 102. The same arrangement for mounting the left side upper jaw holder 103 is followed using screws 121 and 122.

Right and left upper jaw keepers 123 and 124 prevent the upper jaws 6 from dropping down on the inside, because spring pins 126 and 127 are located on the outside and when depressed snap into the holes 128 and 129 of the right side upper jaw holder 102. The same procedure is followed with the left upper jaw keeper 124.

The jaw inserts 8 on the right and left sides of the STR unit 1 and in front of the upper jaws 6 are held in place by inserting threaded bolts 130 and 131 into each insert 8 and through the right and left keepers 123 and 124 and screwing into the upper jaw holders 102 and 103. The spring pins 132 and 133 are included in the lower jaw 7 which when depressed snap into the two holes 15 in the lower jaw holder 16.

Figure 9:
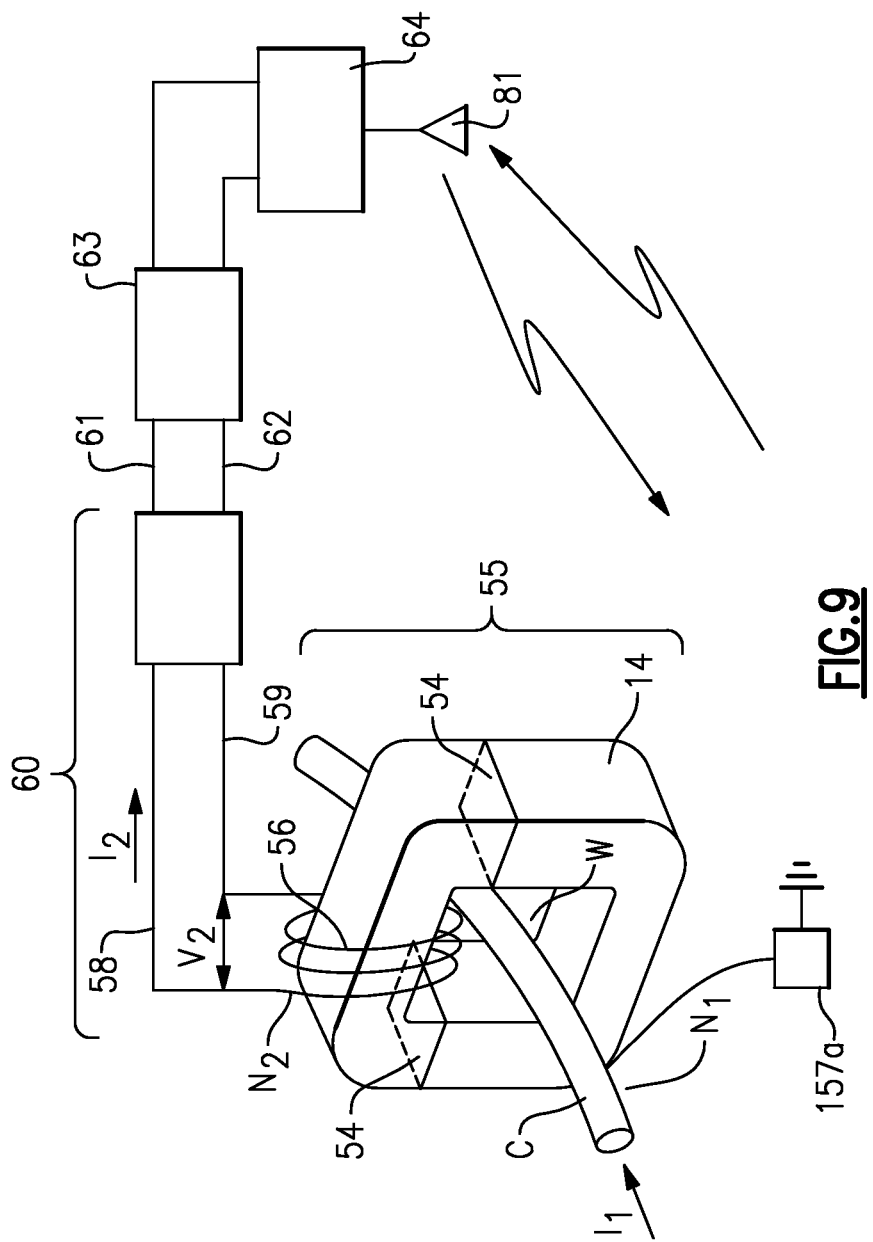
FIG. 9 illustrates a schematic view of the line mounted power supply, electronics and transmitter-receiver of the STR unit.

The transmitting and receiving antenna 81 for the on-board transmitter and receiver 64 shown in FIG. 9 is mounted on the housing 2. The antenna 81 is displayed in FIGS. 1 and 2 and is installed on the top left side in FIG. 1. The solar sensor assembly 134 is located at the top of this housing and on its vertical centerline (FIG. 13). The small hole 140 located directly to the right of the conductor C allows access and adjustment of the electric power line sag sensor 140 (FIG. 1).

All power quantities are derived from the measurements of the voltage (V) and current (I) waveforms and the angle θ between the measured V and I. The real power P, given in watts is the product of the absolute rms values of the voltage |V| and |I| magnitudes times the cosine of the angle θ. The reactive power Q, given in vars is the product of the absolute rms values of |V| and |I| magnitudes times the sine of the angle θ, which is either positive for lagging inductive loads or negative for leading capacitive loads. Therefore, the apparent power is P+jQ. The STR unit 1 measures the current and voltage waveforms for three phase power flows or single phase power, and the phase angle between the current and voltage, or power factor.

Figure 17:
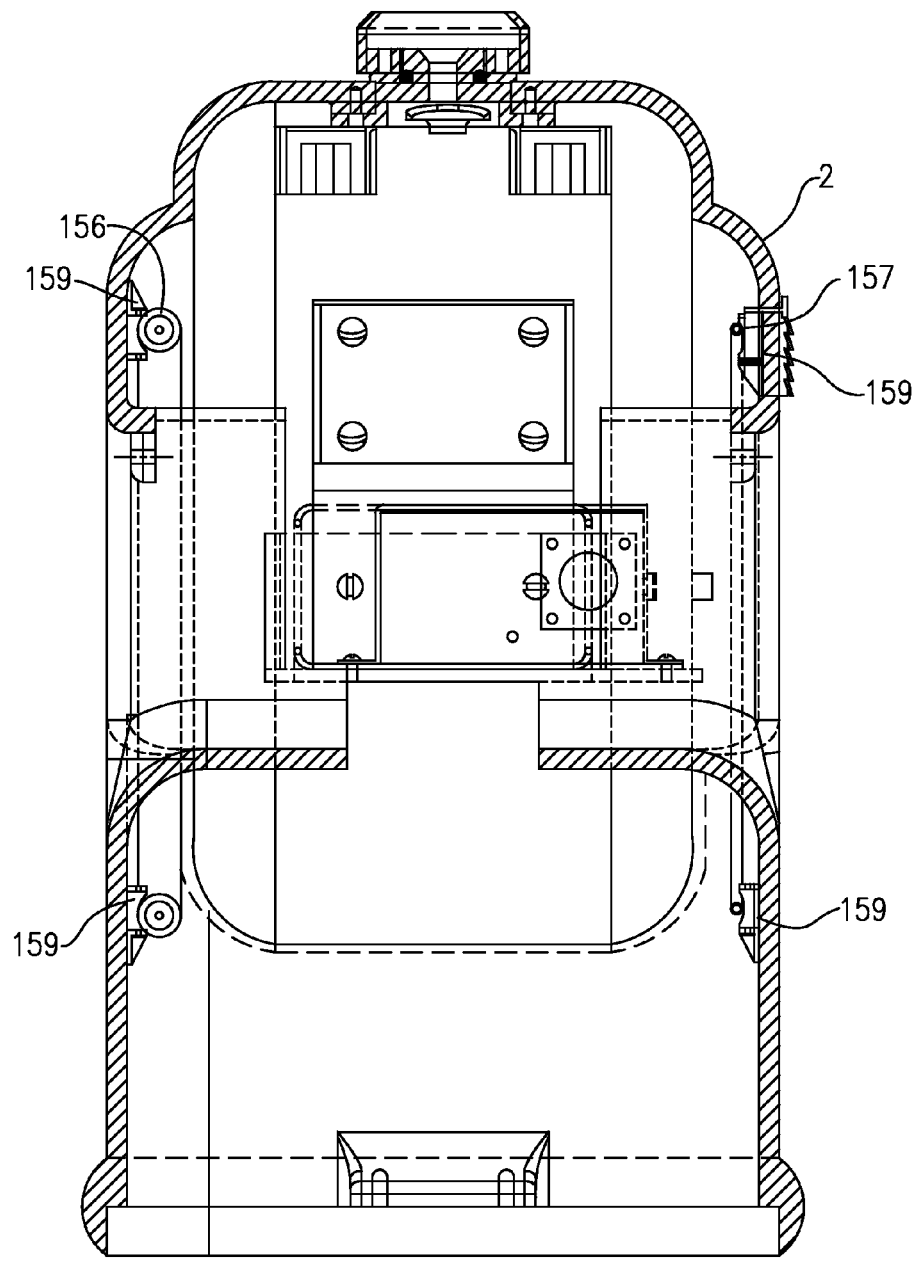
FIG. 17 illustrates a cross-sectional view of the example upper housing showing the "C" loop coil of FIG. 16 and another example "C" loop coil for measuring lightning stroke current taken along line F-F of FIG. 1.

Referring to FIGS. 16 and 17, the "C" loop coils 156 and 157 are mounted inside the upper housing 2 such that a vertical center line of the "C" loop coils 156 and 157 are located on a vertical centerline $C_V$ of the conductor C located within the STR unit 1. As discussed above, the STR unit 1 is adaptable to a full range of conductors C diameter sizes and insures each of the vertical centerlines of the "C" loop coils 156 and 157 extends through the vertical center line of the conductor C. Additionally, the horizontal centerline $C_H$ of the "C" loop coils 156 and 157 may vary up or down from the horizontal centerline $C_H$ of the conductor C. For this design, there may be a maximum offset of plus or minus 0.75 inches as measured up or down from the horizontal centerline of the "C" loop coils 156 and 157 and the horizontal centerline $C_H$ for the majority of conductors C used in the industry, and there is no measureable difference between the measured current flowing in the conductor C and the measured value from the "C" loop coils 156 and 157 current signals. Furthermore, the upper magnetic core 40 and the lower magnetic core 14, which also are located on the vertical centerline of the conductor C and mid-way between the two "C" loop coils 156 and 157, can be moved up or down from the horizontal centerline plus or minus 0.75 inches with no affect on the measured current from the "C" loop coils 156 and 157. In addition, the measured output voltage from the "C" loop coils 156 and 157 and thus the current signal is linear for a full range of conductor current from 10 amperes to 4017 amperes.

Figure 18:
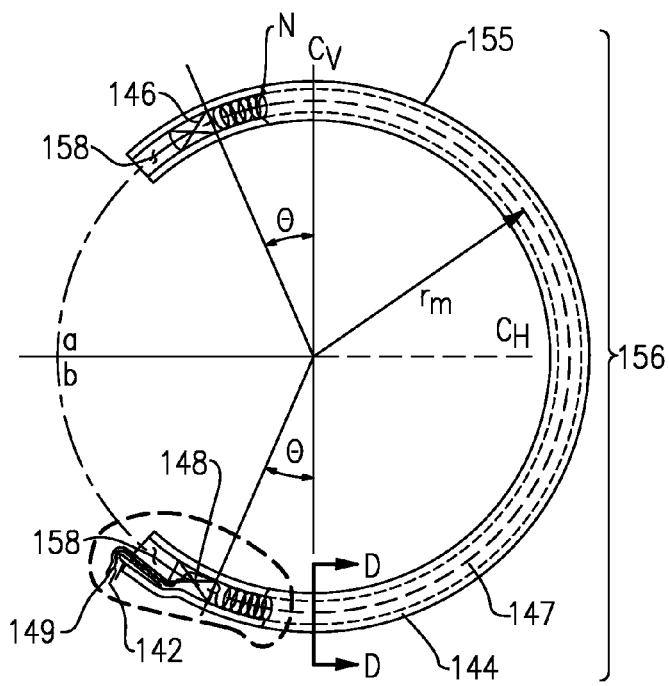
FIG. 18 illustrates a right side view of the example "C" loop coil.

The "C" loop coil 156 of FIG. 18 has an angle θ of 23.4 degrees as measured from the vertical center line $C_V$ of the "C" loop coils 156 and 157 and the conductor C. In another example, the angle θ of the "C" loop coil 156 is between 90 degrees and 0 degrees. Increasing the angle θ increases the number of turns N on the "C" loop coil 156, the voltage output, and thus the measured current signal. For current values as low as 10 amperes through the conductor C, increasing the angle θ may be necessary to obtain an acceptable output voltage from the "C" loop coil 156. The angle θ is set at 23.4 degrees in this example to allow the "C" loop coil 156 to fit over the largest size conductor C anticipated and still fit into the upper housing 2 of the STR unit 1 as shown in FIGS. 16 and 17.

The "C" loop coil 156 has the advantage of being slipped over a conductor C while it is energized at high voltage without shutting the conductor C down. In addition, extraneous magnetic flux from current in the upper magnetic core 40, the lower magnetic core 14, and the power supply transformer 55 does not affect the output voltage and thus the measured current signal from the "C" loop coil 156, even when the power supply transformer 55 windings are shorted. In low to medium voltage distribution circuits with conductor C currents as low as 10 amperes, the output voltage from the "C" loop coil 156 can be doubled by adding a second layer coil wound in the reverse direction from the first layer coil. This design can be used for measuring the conductor C line frequency load current of 60 Hz or 50 Hz, but cannot be used to measure the higher frequency lightning stroke current of from 1 to 10 MHz because the distributed capacitance between the two layers of windings causes phase shift in the measured current signal. A dielectric coil form 145 located within the "C" loop coil 156 can be rigid. This prevents the turns of the first and second coil windings of the double layer winding of the "C" loop coil 156 from rubbing together which avoids failure of the winding insulation had the "C" loop coil been made flexible.

In this example, the "C" loop coil 156 includes the dielectric form 145 which is non-metallic and can be rigid because it is not necessary to bend or flex the "C" loop coil 156 completely around the conductor C to obtain accurate current measurements. In the example shown in FIG. 18, the mean radius of the "C" loop coil 156 is $r_m$ for the conductor C frequency current measurement which fits into the contoured shape of the housing 2.

Figure 19:
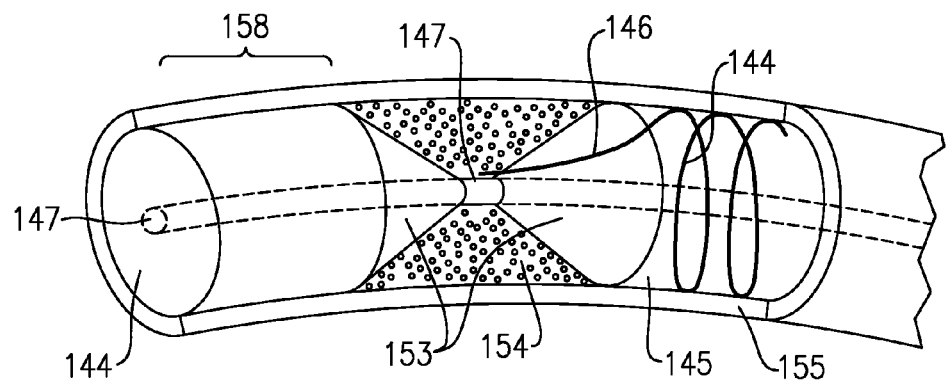
FIG. 19 illustrates a cross-sectional view of a top end of the "C" loop coil of FIG. 18.
Figure 20:
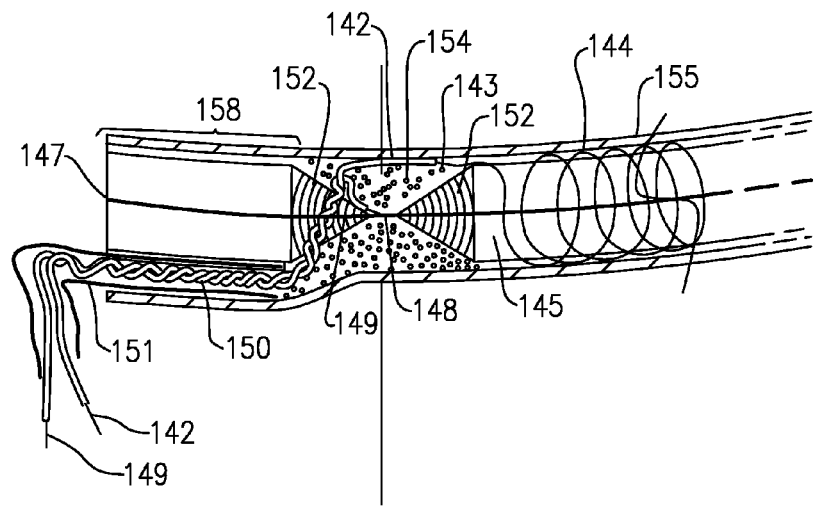
FIG. 20 illustrates a cross-sectional view of a bottom end of the "C" loop coil of FIG. 18.

Referring to FIGS. 18-20, a first insulated lead 142 is connected to the start 143 of a coil wire 144. The coil wire 144 is wound around the dielectric coil form 145. An end 146 of the coil wire 144 is connected to a central conductor 147 (FIG. 19). The central conductor 147 extends through the center of the dielectric coil form 145 and the coil wire 144. An end 148 of the central conductor 147 is connected to a second insulated lead 149 (FIG. 20).

The voltage output of the "C" loop coil 156 is measured between the first insulated lead 142 and the second insulated lead 149. The first insulated lead 142 and the second insulated lead 149 are twisted into a pair of wires 150 to eliminate the affects of extraneous magnetic fields on the voltage output (FIG. 20). In turn, the first and second insulated leads 142 and 149 are protected by an electrostatic shield 151 to eliminate effects of high voltage electric fields created by the conductor C voltage itself. The shielded first and second insulated leads 142 and 149 are routed to the sensor electronics module 63, which converts the voltage output between the first and second insulated leads 142 and 149 into a measured current signal.

The dielectric coil form 145 includes a first pair of conical areas 152 at a first end of the "C" loop coil 156 to provide a smooth transition between the central conductor 147 and the second insulated lead 149 (FIG. 20). A second pair of conical areas 153 at a second end of the "C" loop coil 156 provide a smooth transition between the end of the central conductor 147 and the coil winding 144 (FIG. 19). The connection points adjacent each end of the central conductor 147 are wrapped with several layers of tape or other suitable electric insulating material 154 to make a rigid joint and to reinstitute the dielectric strength of material removed at the first conical area 152 and the second conical area 153 after making the electrical connections to the central conductor 147.

A protective cover 155 may be added over the coil wire 144 to protect the coil wire 144 from becoming abraded during mounting of the "C" loop coil 156 inside the STR unit 1 of the upper housing 2. The protective cover 155 may consist of a heat shrinkable material that covers the coil wire 144, the first and second conical areas 152 and 153, stubs 158 at each end of the dielectric coil form 145, and the pair of wires 150. The "C" loop coils 156 and 157 may be mounted to the housing 2 using mounted brackets 159 attached to the housing 2, of which are in turn attached to the stubs 158, as shown in FIG. 17.

Also, the "C" loop coil 156 can be used to capture the power line frequency alternating current (sinusoidal) waveforms of faults in the power system using the same "C" loop coil 156 used to measure the steady state load current of the conductor C although the current magnitudes are generally much higher than the steady state load current. Because the "C" loop coil 156 includes a winding around a dielectric form, saturation at high currents which would normally happen with traditional iron core current transformers is prevented.

In addition, the "C" loop coil 156 is capable of capturing motor starting currents and capacitor switching currents which are common occurrences on power systems. This is beneficial because traditional iron core current transformers produce a phase shift when measuring current. The "C" loop coil 156 does not produce any measurable phase shift between the current being measured in the conductor C and the "C" loop coil 156 output after integrating the voltage output.

Figure 21:
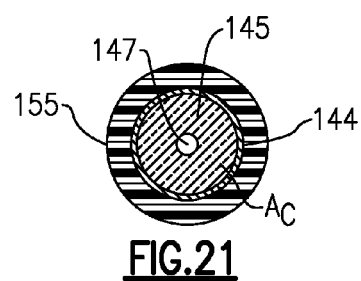
FIG. 21 illustrates a cross-sectional view of the "C" loop coil of FIG. 18 taken along line D-D of FIG. 18.
Figure 22:
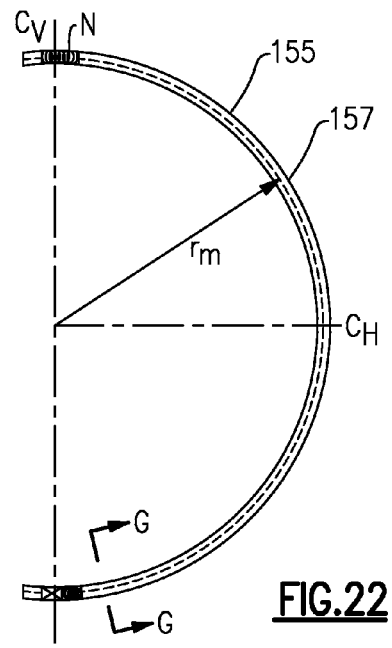
FIG. 22 illustrates a right side view of the other example "C" loop coil, used for measuring lightning stroke current.

Referring to FIGS. 17 and 21-22, the "C" loop coil 157 is similar to the "C" loop coil 156 except where discussed below and shown in FIGS. 17, and 21-22. The "C" loop coil 157 is used for lightning stroke current measurements. The coil cross section area $A_C$ and the number of turns N may need to be reduced to minimize the high output voltages compared to the "C" loop coil 156 because of the high rate of change of lightning stroke current. Therefore, the angle θ may be reduced to zero degrees as shown in FIG. 22 to minimize the number of turns N in the "C" loop coil 157 for measuring lightning stroke currents. If the output voltages for the "C" loop coil 157 are still too high for lightning strokes of 200 kA or higher, then the angle θ can be reduced to a negative angle. In order to assure high accuracy lightning stroke measurements with the "C" loop coil 157, the "C" loop coil 157 must be placed on the vertical centerline $C_V$ of the conductor C. This is also the case for the measurements of normal conductor C power line frequency (50 $H_Z$ and 60 $H_Z$) steady state load currents, and high magnitude sinusoidal fault currents. The "C" loop coil 157 is mounted in a similar fashion, as the "C" loop coil 156 (FIG. 17). With the "C" loop coil 157, the phase shift between the actual lightning stroke current and the measured current in the conductor C is less than 0.26 degrees even for a lightning stroke frequency of 1 MHz.

Another advantage of the "C" loop coil 156 is the cross sectional area $A_C$ of the "C" loop coil 156 can be made large enough to measure low conductor currents of 10 amperes or less. Since a large cross sectional area $A_C$ makes the "C" loop coil 156 become very stiff, this option is not available in prior art devices that require flexing the loop to open and close the loop completely around the conductor C. Since the "C" loop coil 156 is not bent completely around the conductor C, the "C" loop coil 156 can be rigid.

The sensor electronics module 63 receives data from the "C" loop coils 156 and 157, processes the data, and sends the data to the transmitter-receiver unit 64, which sends the data to at least one remote location via the antenna 81.

The sensor electronics module 63 calculates the total harmonic distortion of the current and the real time thermal capacity of the conductor C. Since the sensor electronics module 63 collects the measured current for three phase power systems, the percent of unbalanced current can be calculated. The percent of unbalanced current is calculated by dividing the negative sequence current $I_2$ by the positive sequence current $I_1$. The negative and positive sequence current $I_1$ and $I_2$ are derived from the measured "C" loop coil 156 current waveforms and the resultant phasor magnitudes and angles between each phasor.

The sensor electronics module 63 records the fault current waveforms based on detecting a depression in the post fault voltage and the angle between the voltage and fault current. The fault current direction is found by comparing the polarity of a prefault load current with a post fault current. If there is a change in polarity between the prefault load current and the post fault load current, then the fault current is in the opposite direction to the prefault load current. If there is no change in polarity, the fault current is in the same direction as the prefault load current. This feature allows the sensor electronics module 63 to determine the direction of the fault current obtained from the "C" loop coil 156 of different STR units 1 mounted on the conductor C to pin point the location of the fault along the conductor C. In addition, the fault data collected by the "C" loop coil 156 and the sensor electronics module 63 in each of the STR units 1 can send a transfer trip signal to disconnect electric power equipment and generation interconnected to the power system which otherwise are unable to detect a fault has occurred, but yet are required by the electric power utility to disconnect from the power system during faults.

With multiple spaced apart STR units 1 each including the "C" loop coil 156 mounted on the same power line conductor C, the approximate location of the fault can be determined. If the fault current direction measured by each of two adjacent "C" loop coils 156 is pointing in the opposite directions and toward each other, then the fault is located between the two adjacent "C" loop coils 156. If the fault current direction measured by each of the two adjacent "C" loop coils is pointing in the same direction, but opposite to the direction of the prefault load current, then the fault is upstream from the two adjacent "C" loop coils. However, if the fault current direction measured by each of the two adjacent "C" loop coils is pointing in the same direction as the prefault load current, then the fault is downstream from the two adjacent "C" loop coils 156.

To further aid maintenance personnel in determining the actual physical location of a fault due to lightning on the conductor C, the multiple STR units 1 each include the "C" loop coil 157. Each of the "C" loop coils 157 is mounted on the same power line conductor C to measure the polarity and direction of the high magnitude lightning stroke current by comparing the lightning stroke current waveform and its voltage waveform. The voltage waveform is measured with an example voltage measuring device 157a attached to the conductor C and an electrical ground as shown in FIG. 9. Furthermore, lightning stroke current and voltage data are also transmitted to at least one remote location.

Since the STR unit 1 includes the transmitter-receiver unit 64, the STR unit 1 may transmit and receive data to and from remote locations as shown in FIG. 9. Trigger levels for various parameters measured by the STR unit 1 and instructions for responding to the trigger levels can be sent to the transmitter-receiver unit 64 via the antenna 81 by a remote transmitter. The trigger levels and instructions are sent to the sensor electronics module 63 and are stored in a data storage device. The trigger levels are either fixed values or rate of change values of a particular parameter measured by the STR unit 1. Once a parameter meets the fixed value or rate of change value, the instructions embedded in the software on the data storage device in the sensor electronics module 63 determines whether or not to transmit the data.

For example, the trigger levels and instructions include a sample rate of change and the integration period of the data that can be increased or decreased. The sensor electronics module 63 can also utilize trigger values to determine when steady state collected data is changed to transient state collected data.

In another example, when the measured steady state current data abruptly increases in magnitude and the measured steady state voltage data abruptly decreases in magnitude based on preset trigger values and instructions from the transmitter-receiver unit 64 of the STR unit 1, the event indicates a fault. Data from the event can be sent to the remote location in the form of a transfer trip signal to disconnect devices such as distributed generators in the power system. Furthermore, when the fault in the power system has been corrected by electric utility protective devices, then the STR unit 1 can send another signal to the disconnected devices to re-connect them to the power system. As shown in FIG. 13, the STR unit 1 contains an energy storage device 256 (i.e. capacitor) that stores energy which is used to power the STR unit 1 when the utility has interrupted the current in the power line conductor, and allows the unit to transmit fault date to the at least one remote location.

The preceding description is exemplary rather than limiting in nature. Variations and modifications to the disclosed examples may become apparent to those skilled in the art that do not necessarily depart from the essence of this disclosure. The scope of legal protection given to this disclosure can only be determined by studying the following claims.

What is claimed is:

1. A device for measuring current of an electric power line conductor comprising:
    a housing including an opening for accepting a power line conductor;
    a first coil loop including coil windings with a first end spaced from a second end and having a circular shape and configured to partially surround the power line conductor located in the housing and an internal central wire attached to an end of the first coil loop and extending through a center of the first coil loop; and a jaw assembly configured to insure a vertical centerline of the first coil loop is aligned with a vertical centerline of the electric power line conductor, wherein the first end of the first coil loop is rigidly fixed from movement relative to the second end of the first coil loop when the jaw assembly moves between an open position for accepting the power line conductor and a closed position for engaging the power line conductor.

2. The device of claim 1, wherein first coil loop defines a circular arc less than 360 degrees.

3. The device of claim 1, including a power supply transformer mounted on the power line conductor adjacent the first coil loop configured to supply power to a sensor electronics module and a transmitter-receiver unit, wherein the power supply transformer includes a first magnetic core slidably attached to a first jaw assembly and a second magnetic core rigidly attached to a second jaw assembly, the first magnetic core and the second magnetic core are configured to surround the power line and move together in unison when in contact.

4. The device of claim 3, wherein the sensor electronics module is configured to convert the voltage output of the first coil loop to a current signal which is representative of a power line frequency current in the electric power line conductor without phase shift and saturation during faults.

5. The device of claim 1, wherein the first coil loop includes a double layer coil loop with windings extending in opposite directions.

6. The device of claim 1, including a second coil loop with a first end spaced from a second end and having a circular arc shape and configured to partially surround the power line conductor located in the housing and a second internal central wire attached to the first end of the second coil loop and extending through a center of the second coil loop, wherein the first end of the second coil loop is rigidly fixed from movement relative to the second end of the second coil loop when the jaw assembly moves between an open position for accepting the power line conductor and a closed position for engaging the power line conductor.

7. The device of claim 6, wherein the second coil loop extends approximately 180 degrees or less.

8. The device of claim 6, including a power supply transformer mounted on the power line conductor adjacent the second coil loop configured to supply power to a sensor electronics module and a transmitter-receiver unit.

9. The device of claim 7, wherein the voltage measured output from the second coil loop is converted to a current signal and is representative of the actual high frequency lightning stroke current flowing in the power line conductor for positive or negative polarity strokes and without phase shift or saturation.

10. The device of claim 6, wherein the second coil loop is mounted to the housing and a vertical centerline of the second coil loop is configured to align with a vertical centerline of the power line conductor.

11. The device of claim 6, wherein the second coil loop is wound on a rigid nonflexible non-metallic dielectric coil form.

12. The device of claim 6, including a first pair of conical areas located at a first end of the second coil loop and a second pair of conical areas located at a second end of the second coil loop.

13. The device of claim 3, including a sensor electronics module configured to process data to determine a fault and a transmitter-receiver unit configured to send data indicating a fault in the power line conductor to at least one remote location.

14. The device of claim 13, wherein the transmitter-receiver unit is configured to receive trigger data from at least one remote location.

15. The device of claim 13, including an energy storage device configured to supply power to the sensor electronics module and the transmitter-receiver unit.

16. The device of claim 1, including a voltage measuring device configured to determine a location of a lighting stroke.

17. The device of claim 1, wherein the opening extends through a rigidly fixed portion of the housing.

18. The device of claim 17, wherein the housing includes a one piece first portion and a one piece second portion, the opening extends through the one piece first portion.

19. The device of claim 18, wherein the jaw assembly includes a first jaw assembly and a second jaw assembly, the first jaw assembly and the second jaw assembly are located within the first portion of the housing and are configured to engage the power line conductor, the first jaw assembly is fixed relative to the first portion of the housing and the second jaw assembly is movable relative to first portion of the housing.

20. The device of claim 2, wherein first coil loop defines a circular arc greater than 180 degrees.

21. The device of claim 1, wherein the first coil loop is wound on a rigid nonflexible non-metallic dielectric coil form.

22. The device of claim 1, including a first pair of conical areas located at a first end of the first coil loop and a second pair of conical areas located at a second end of the first coil loop.

23. A device for measuring current of an electric power line conductor comprising:
   a housing including an opening for accepting a power line conductor;
   a first coil loop including coil windings with a first end spaced from a second end and having a circular shape and configured to partially surround the power line conductor located in the housing and an internal central wire attached to an end of the first coil loop and extending through a center of the first coil loop, and the first end of the first coil loop is rigidly fixed from movement relative to the second end of the first coil loop; and
   a jaw assembly configured to insure a vertical centerline of the first coil loop is aligned with a vertical centerline of the electric power line conductor, wherein the first coil loop is wound on a rigid nonflexible non-metallic dielectric coil form.

24. A device for measuring current of an electric power line conductor comprising:
   a housing including an opening for accepting a power line conductor;
   a first coil loop including coil windings with a first end spaced from a second end and having a circular shape and configured to partially surround the power line conductor located in the housing and an internal central wire attached to an end of the first coil loop and extending through a center of the first coil loop, and the first end of the first coil loop is rigidly fixed from movement relative to the second end of the first coil loop;
   a jaw assembly configured to insure a vertical centerline of the first coil loop is aligned with a vertical centerline of the electric power line conductor; and a first pair of conical areas located at a first end of the first coil loop and a second pair of conical areas located at a second end of the first coil loop.

\* \* \* \* \*